United States Patent
Cho et al.

(10) Patent No.: US 12,258,306 B2
(45) Date of Patent: Mar. 25, 2025

(54) DIAMINE, POLYMER AND FILM PRODUCED USING THE SAME

(71) Applicants: SK Innovation Co., Ltd., Seoul (KR); SK ie technology Co., Ltd., Seoul (KR)

(72) Inventors: Hyun Kyu Cho, Daejeon (KR); Jin Hyung Park, Daejeon (KR); Hyo Shin Kwak, Daejeon (KR); Seung Min Jeon, Daejeon (KR); Jong Chan Kim, Daejeon (KR); Joo Hyun Lee, Daejeon (KR)

(73) Assignees: SK Innovation Co., Ltd., Seoul (KR); SK ie technology Co., Ltd., Seoul (KR)

( * ) Notice: Subject to any disclaimer, the term of this patent is extended or adjusted under 35 U.S.C. 154(b) by 279 days.

(21) Appl. No.: 17/957,519

(22) Filed: Sep. 30, 2022

(65) Prior Publication Data

US 2023/0123199 A1    Apr. 20, 2023

(30) Foreign Application Priority Data

Oct. 1, 2021 (KR) .................. 10-2021-0130533
Oct. 18, 2021 (KR) .................. 10-2021-0138409

(51) Int. Cl.
  C07C 237/40    (2006.01)
  C08G 69/32     (2006.01)
  C08G 73/10     (2006.01)
  C08G 73/14     (2006.01)
  C08J 5/18      (2006.01)

(52) U.S. Cl.
  CPC ............ *C07C 237/40* (2013.01); *C08G 69/32* (2013.01); *C08G 73/1039* (2013.01); *C08G 73/1042* (2013.01); *C08G 73/1067* (2013.01); *C08G 73/1078* (2013.01); *C08G 73/14* (2013.01); *C08J 5/18* (2013.01); *C08J 2377/10* (2013.01); *C08J 2379/08* (2013.01)

(58) Field of Classification Search
  CPC .. C07C 237/40; C08G 69/32; C08G 73/1039; C08G 73/1042; C08G 73/1067; C08G 73/1078; C08G 73/14; C08J 5/18; C08J 2377/10; C08J 2379/08
  See application file for complete search history.

(56) References Cited

U.S. PATENT DOCUMENTS

| | | | |
|---|---|---|---|
| 2015/0011726 A1* | 1/2015 | Hasegawa | G02B 5/20 528/322 |
| 2017/0342224 A1 | 11/2017 | Chae et al. | |
| 2021/0324145 A1 | 10/2021 | Ahn et al. | |
| 2023/0174717 A1* | 6/2023 | Wang | C08G 73/1028 528/350 |

FOREIGN PATENT DOCUMENTS

| | | | | |
|---|---|---|---|---|
| CN | 112079743 A | | 12/2020 | |
| CN | 115784923 A | * | 3/2023 | |
| JP | 2005255981 A | * | 9/2005 | |
| JP | 2018193343 A | | 12/2018 | |
| KR | 1020090070093 A | | 7/2009 | |
| KR | 1020140114798 A | | 9/2014 | |
| KR | 1020170132499 A | | 12/2017 | |
| KR | 1020190102299 A | | 9/2019 | |
| KR | 102219707 B1 | | 2/2021 | |
| WO | WO-2016152928 A1 | * | 9/2016 | .......... C07C 211/50 |

* cited by examiner

*Primary Examiner* — John D Freeman
(74) *Attorney, Agent, or Firm* — The Webb Law Firm

(57) ABSTRACT

The present invention relates to a diamine, and a polymer and film produced using the same. Specifically, the diamine may be significantly effectively used as a monomer for producing a polyimide-based film that is colorless and transparent and has improved mechanical strength.

21 Claims, No Drawings

DIAMINE, POLYMER AND FILM PRODUCED USING THE SAME

CROSS-REFERENCE TO RELATED APPLICATIONS

This application claims priority to Korean Patent Application No. 10-2021-0130533 filed Oct. 1, 2021, and No. 10-2021-0138409 filed Oct. 18, 2021, the disclosures of which are hereby incorporated by reference in their entirety.

BACKGROUND OF THE INVENTION

Field of the Invention

The following disclosure relates to a diamine, which is a monomer effectively used for producing a polyimide-based film, and a polymer and film produced using the same.

Description of Related Art

Recently, as weight reduction, slimness, and flexibility of a display device become important, studies have been actively conducted to replace a glass substrate, cover glass, and the like, which have been widely used in a display device in the related art, with polyimide. In order to apply polyimide to a next-generation display device, it is required to secure excellent optical properties and also to improve mechanical properties. Therefore, the required performance for a polyimide-based polymer for a display device has been gradually advanced.

To this end, studies have been conducted to improve mechanical properties by combining a colorless polyimide (CPI)-based resin with a monomer having strong straightness and rigidity or introducing an amide group. However, there is a trade-off relationship between the optical properties and the mechanical properties of the polyimide-based film. Therefore, these attempts have a limitation in that the optical properties of the polyimide-based film are deteriorated even though the mechanical properties of the polyimide-based film are improved. In addition, since solution handleability of the polyimide-based resin is deteriorated, the difficulty of the process may be increased, or the resin may not be obtained.

Therefore, there is a demand for development of a polyimide-based film that may be widely applied by implementing improved mechanical properties, in particular, an excellent modulus, without deterioration of the colorless and transparent performance.

SUMMARY OF THE INVENTION

An embodiment is directed to providing a diamine, which is a monomer for providing a polyimide-based film capable of simultaneously implementing excellent optical properties and mechanical properties, and a method of preparing the same.

Another embodiment is directed to providing a polymer produced using the diamine and a high-strength, colorless, and transparent polyimide-based film produced using the diamine.

Still another embodiment is directed to providing a multilayer structure including the polyimide-based film and a display device including the polyimide-based film.

In one general aspect, there is provided a diamine represented by the following Chemical Formula 1:

[Chemical Formula 1]

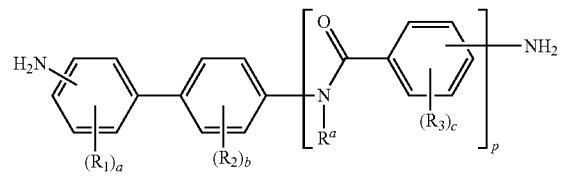

in Chemical Formula 1,
$R_1$ and $R_2$ are each independently (C2-C20) alkyl, (C1-C20) alkoxy, halo (C1-C20) alkyl, (C1-C20) alkylcarbonyl, (C1-C20) alkoxycarbonyl, (C6-C20) arylcarbonyl, tri(C1-C20) alkylsilyl, carboxyl, hydroxy, amino, nitro, cyano, or halogen;
$R_3$ is (C1-C20) alkyl, (C1-C20) alkoxy, halo (C1-C20) alkyl, (C1-C20) alkylcarbonyl, (C1-C20) alkoxycarbonyl, (C6-C20) arylcarbonyl, tri(C1-C20) alkylsilyl, carboxyl, hydroxy, amino, nitro, cyano, or halogen;
$R^a$ is hydrogen, (C1-C20) alkyl, or (C6-C20) aryl;
a and b are each independently an integer of 1 to 4;
c is an integer of 0 to 4;
when a, b, and c are integers of 2 or more, $R_1$, $R_2$, and $R_3$ may be the same as or different from each other; and
p is an integer of 1 to 3.

The diamine represented by Chemical Formula 1 may be represented by the following Chemical Formula 2 or 3:

[Chemical Formula 2]

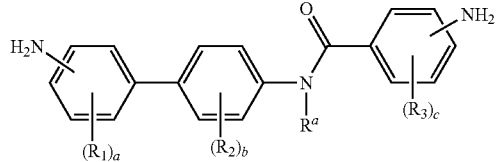

[Chemical Formula 3]

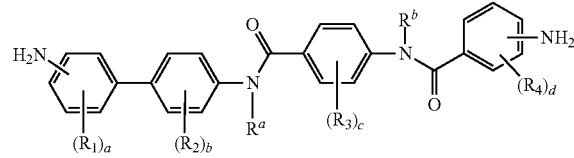

in Chemical Formulas 2 and 3,
$R_1$ and $R_2$ are each independently (C2-C7) alkyl, (C1-C7) alkoxy, halo (C1-C7) alkyl, (C1-C7) alkylcarbonyl, (C1-C7) alkoxycarbonyl, (C6-C12) arylcarbonyl, tri (C1-C7) alkylsilyl, carboxyl, hydroxy, amino, nitro, cyano, or halogen;
$R_3$ and $R_4$ are each independently (C1-C7) alkyl, (C1-C7) alkoxy, halo (C1-C7) alkyl, (C1-C7) alkylcarbonyl, (C1-C7) alkoxycarbonyl, (C6-C12) arylcarbonyl, tri (C1-C7) alkylsilyl, carboxyl, hydroxy, amino, nitro, cyano, or halogen;
$R^a$ and $R^b$ are each independently hydrogen, (C1-C7) alkyl, or (C6-C12) aryl;
a and b are each independently an integer of 1 to 3;
c and d are each independently an integer of 0 to 3; and
when a, b, c, and d are integers of 2 or more, $R_1$, $R_2$, $R_3$, and $R_4$ may be the same as or different from each other.

The diamine represented by Chemical Formula 1 may be represented by the following Chemical Formula 4 or 5:

[Chemical Formula 4]

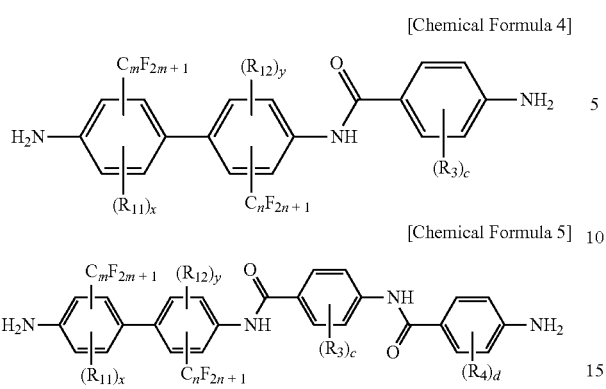

[Chemical Formula 5]

in Chemical Formulas 4 and 5,
$R_3$ and $R_4$ are each independently (C1-C7) alkyl, (C1-C7) alkoxy, halo (C1-C7) alkyl, carboxyl, hydroxy, amino, or halogen;
$R_{11}$ and $R_{12}$ are each independently (C2-C7) alkyl, halo (C1-C7) alkyl, or halogen;
n and m are each independently an integer of 1 to 5;
x, y, c, and d are each independently an integer of 0 to 2; and
when x, y, c, and d are 2, $R_{11}$, $R_{12}$, $R_3$, and $R_4$ may be the same as or different from each other.

The diamine represented by Chemical Formula 1 may be represented by the following Chemical Formula 6 or 7:

[Chemical Formula 6]

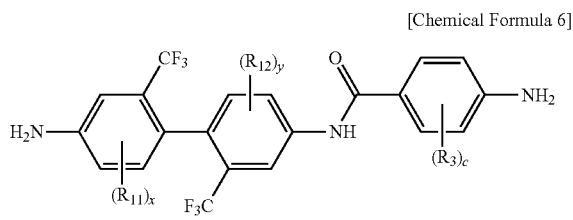

[Chemical Formula 7]

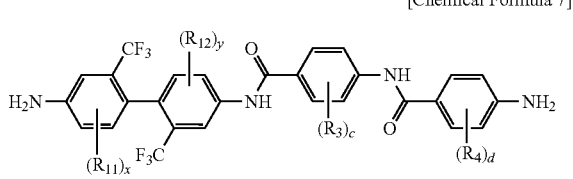

in Chemical Formulas 6 and 7,
$R_3$ and $R_4$ are each independently (C1-C5) alkyl, (C1-C5) alkoxy, halo (C1-C5) alkyl, carboxyl, hydroxy, amino, or halogen;
$R_{11}$ and $R_{12}$ are each independently (C2-C5) alkyl, halo (C1-C5) alkyl, or halogen;
x, y, and d are each independently 0 or 1; and
c is an integer of 0 to 2.

The diamine may be selected from the following compounds:

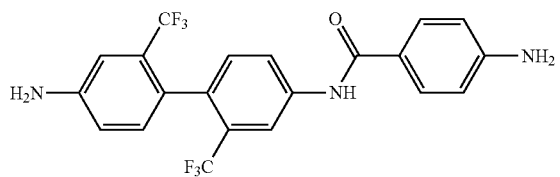

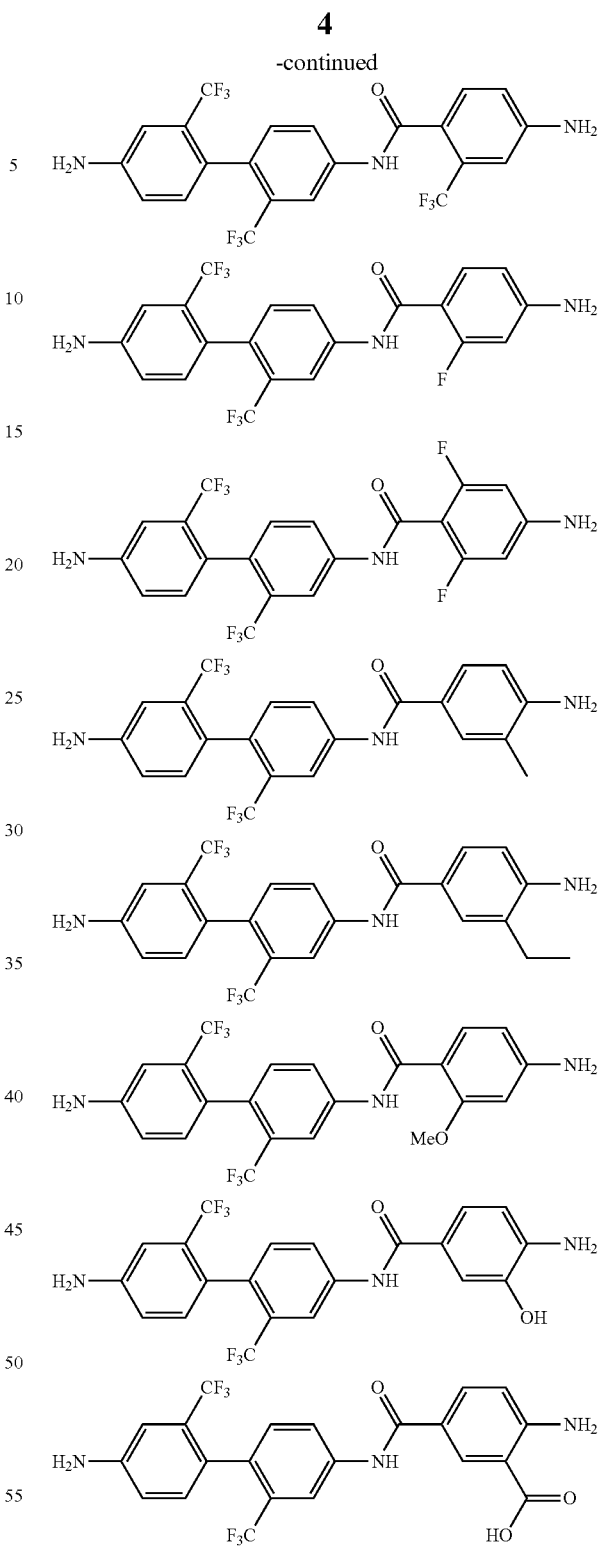

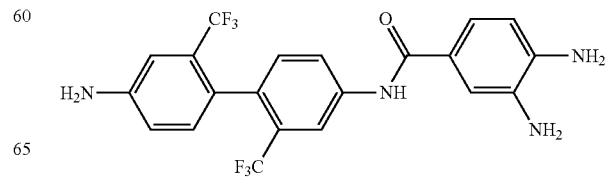

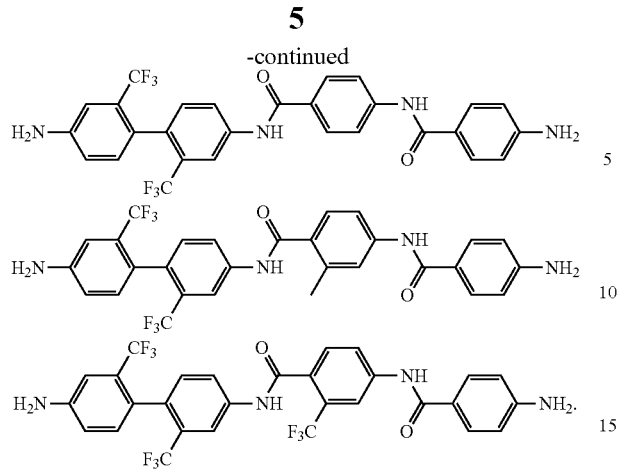

In another general aspect, a method of preparing a diamine includes preparing a diamine represented by the following Chemical Formula 1 by reducing a compound represented by the following Chemical Formula A under a reduction catalyst:

[Chemical Formula 1]

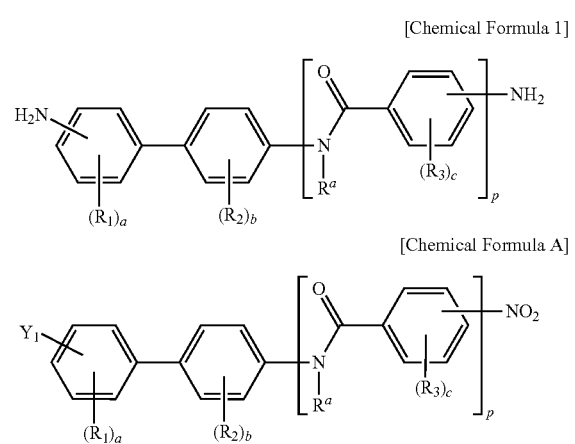

[Chemical Formula A]

in Chemical Formulas 1 and A,
$Y_1$ is nitro or amino; and
the definitions of $R_1$ to $R_3$, $R^a$, a, b, c, and p are the same as those in Chemical Formula 1.

The reduction catalyst may be selected from Zn, Cu, Ag, Au, Cd, Hg, Fe, $K_4[Fe(CN)_6]$, $NaBH_4$, and a combination thereof.

The reduction catalyst may further include a cocatalyst selected from $NH_4Cl$, $H_2CO_3$, $H_3PO_4$, HCl, $CH_3COOH$, and a combination thereof.

The compound represented by Chemical Formula A may be prepared by reacting $Y_2$ of a compound represented by the following Chemical Formula A-1 with X of a compound represented by the following Chemical Formula A-2:

[Chemical Formula A]

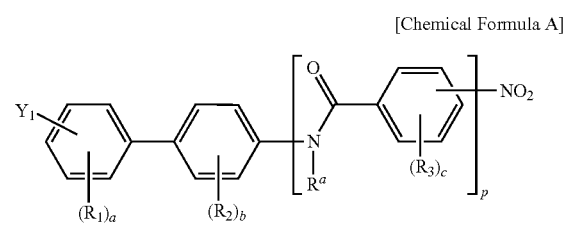

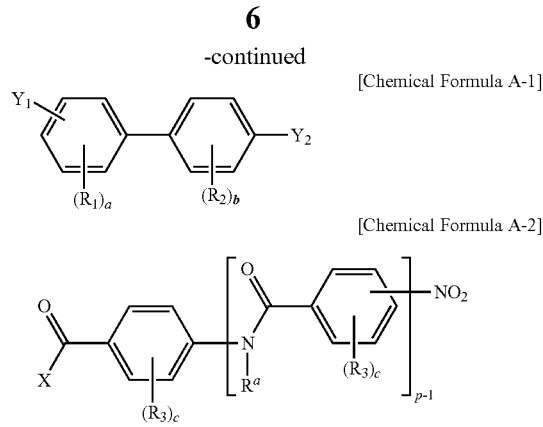

in Chemical Formulas A, A-1, and A-2,
X is halogen;
$Y_1$ is nitro or amino;
$Y_2$ is $$*\!\!-\!\!NHR^a \text{ or } *\!\!-\!\!\overset{+}{N}H_2R^a;$$

and
the definitions of $R_1$ to $R_3$, $R^a$, a, b, c, and p are the same as those in Chemical Formula 1.

In still another general aspect, a polymer has a structural unit derived from the diamine; and a structural unit derived from a dianhydride, a structural unit derived from an aromatic diacid dichloride, or a combination thereof.

The dianhydride may include a fluorine-based aromatic dianhydride and an alicyclic dianhydride.

The aromatic diacid dichloride may include terephthaloyl dichloride, isophthaloyl dichloride, 1,1'-biphenyl-4,4'-dicarbonyl dichloride, 1,4-naphthalenedicarboxylic dichloride, 2,6-naphthalenedicarboxylic dichloride, 1,5-naphthalenedicarboxylic dichloride, 4,4'-oxybis(benzoyl chloride), or a combination thereof.

In still another general aspect, a composition for forming a film contains the polymer.

In still another general aspect, there is provided a film produced using the composition for forming a film.

The film may include polyimide, polyamide, or a combination thereof.

A thickness of the film may be 1 to 500 um.

The film may have a yellow index (YI) of 10 or less when measured according to ASTM E313, a haze of 2.0% or less when measured according to ASTM D1003, and a total light transmittance of 80% or more when measured according to ASTM D1003.

The film may have a modulus of 5 GPa or more when measured according to ASTM D882.

In still another general aspect, a multi-layer structure includes the film.

In still another general aspect, a display device includes the film.

Other features and aspects will be apparent from the following detailed description, the drawings, and the claims.

DESCRIPTION OF THE INVENTION

Unless otherwise defined, all the technical terms and scientific terms used in the present invention have the same meanings as commonly understood by those skilled in the art to which the present invention pertains. The terms used in the description of the present invention are merely used to effectively describe a specific exemplary embodiment, but are not intended to limit the present invention.

Unless the context clearly indicates otherwise, singular forms used in the present specification may be intended to include plural forms.

In addition, units used in the present specification without special mention are based on weight, and as an example, a unit of % or a ratio means wt % or a weight ratio. Unless otherwise defined, wt % means wt % of any one component in a composition with respect to the total weight of the composition.

In addition, a numerical range used in the present specification includes upper and lower limits and all values within these limits, increments logically derived from a form and span of a defined range, all double limited values, and all possible combinations of the upper and lower limits in the numerical range defined in different forms. Unless otherwise specifically defined in the specification of the present invention, values out of the numerical ranges that may occur due to experimental errors or rounded values also fall within the defined numerical ranges.

In the present specification, the expression "comprise(s)" is intended to be an open-ended transitional phrase having an equivalent meaning to "include(s)," "contain(s)," "have (has)," and "are (is) characterized by," and does not exclude elements, materials, or steps, all of which are not further recited herein.

In the present specification, the term "A and/or B" may mean an aspect including both A and B, and may mean an aspect selected from A and B.

In the present specification, the term "polymer" includes an oligomer, and includes a homopolymer and a copolymer. The copolymer may include an alternating copolymer, a block copolymer, a random copolymer, a branched copolymer, a crosslinked copolymer, or a copolymer including all of these copolymers.

In the present specification, the term "polyamic acid" may mean a polymer having a structural unit having an amic acid moiety, the term "polyimide" may mean a polymer having a structural unit having an imide moiety, the term "polyamide" may mean a polymer having a structural unit having an amide moiety, and the term "polyamideimide" may mean a polymer having a structural unit having an imide moiety and an amide moiety.

In the present specification, the term "polyimide precursor solution" may have an equivalent meaning to a "polyamic acid solution", and may mean a solution containing polyimide and/or polyamic acid. In addition, the "polyimide" may be used to include polyimide or polyamideimide, and the "polyamic acid" may be used to include polyamic acid or poly(amide-amic acid).

In the present specification, the term "polyimide-based film" may be used to include a polyimide film or a polyamideimide film.

In the present specification, the term "halogen" may mean a fluorine (F), chloride (Cl), bromine (Br), or iodine (I) atom.

In the present specification, the term "alkyl" may be an organic radical derived from an aliphatic hydrocarbon by removing one hydrogen atom, and may include both linear and branched forms. The alkyl may have 1 to 20 carbon atoms, specifically, 1 to 15 carbon atoms, more specifically, 1 to 10 carbon atoms, still more specifically, 1 to 7 carbon atoms, and still more specifically, 1 to 5 carbon atoms. Examples of the alkyl include, but are not limited to, methyl, ethyl, propyl, isopropyl, butyl, isobutyl, t-butyl, pentyl, hexyl, and ethylhexyl.

In the present specification, the term "alkoxy" is represented by *—O-alkyl, where the alkyl is the same as defined above. Examples of the alkoxy include, but are not limited to, methoxy, ethoxy, n-propoxy, isopropoxy, n-butoxy, isobutoxy, and t-butoxy.

In the present specification, the term "haloalkyl" may mean the alkyl in which at least one hydrogen is substituted with halogen.

In the present specification, the term "alkylcarbonyl" means a *—C(=O)alkyl radical, where the alkyl is the same as defined above. Examples of the alkylcarbonyl radical include, but are not limited to, methyl carbonyl, ethyl carbonyl, isopropyl carbonyl, propyl carbonyl, butyl carbonyl, isobutyl carbonyl, and t-butyl carbonyl.

In the present specification, the term "alkoxycarbonyl" means a *—C(=O)alkoxy radical, where the alkoxy is the same as defined above. Examples of the alkoxycarbonyl include, but are not limited to, methoxycarbonyl, ethoxycarbonyl, isopropoxycarbonyl, n-propoxycarbonyl, n-butoxycarbonyl, isobutoxycarbonyl, and t-butoxycarbonyl.

In the present specification, the term "trialkylsilyl" means a *—Si(alkyl)(alkyl)(alkyl) radical, where the alkyl is the same as defined above.

In the present specification, the term "aryl" may be an organic radical derived from an aromatic hydrocarbon by removal of one hydrogen, may include a monocyclic or fused ring system having suitably 4 to 7 ring atoms, and preferably 5 or 6 ring atoms in each ring, and even may include a form in which a plurality of aryls are linked by a single bond. Examples of the aryl include, but are not limited to, phenyl, naphthyl, biphenyl, and terphenyl.

In the present specification, the term "arylcarbonyl" means a *—C(=O)aryl radical, where the aryl is the same as defined above. Examples of the arylcarbonyl include, but are not limited to, phenylcarbonyl, naphthylcarbonyl, and anthrylcarbonyl.

In the present specification, the term "cyano" may mean —CN, the term "nitro" may mean —$NO_2$, the term "hydroxy" may mean —OH, the term "amino" may mean —$NH_2$, and the term "carboxyl" may mean —COOH.

In order for a polyimide film to be applied to a display device, a specific yellow index of the polyimide film should be improved, and colorless and transparent performance should be secured, and mechanical properties should be also improved. However, in order to improve the mechanical properties of a film, in a case where a film is produced using a compound having a rigid structure or a polymer into which an amide structure is introduced, although the mechanical properties are improved, optical properties such as a yellow index, a haze, and a transmittance are deteriorated. Therefore, there is a need for a diamine capable of significantly improving mechanical properties of a transparent polyimide film while maintaining excellent optical properties of the transparent polyimide film.

A diamine according to an exemplary embodiment may improve mechanical strength of a film because it includes a plurality of aromatic rings, and also may reduce crystallinity and a charge transfer complex (CTC) effect because it has an asymmetric structure. That is, the diamine according to an exemplary embodiment may provide a film having significantly improved mechanical properties without deterioration of optical properties, and specifically, a film including polyimide, polyamide, or a combination thereof.

The aromatic ring may include a single ring; an unfused ring in which two or more aromatic rings are linked by a single bond, a substituted or unsubstituted C1 to C5 alkylene group, O, or C(=O); or a combination thereof. Specifically, the aromatic ring may include benzene, biphenyl, or a combination thereof.

As an example, in the diamine, the aromatic ring may include at least one benzene and at least one biphenyl, the aromatic rings may be linked to each other by an amide group, and specifically, the diamine may be represented by the following Chemical Formula 1:

[Chemical Formula 1]

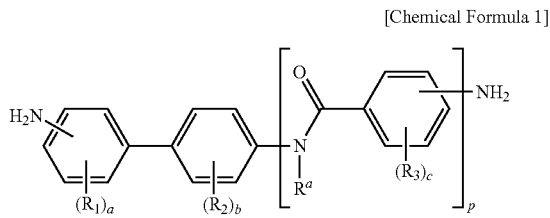

in Chemical Formula 1, $R_1$ and $R_2$ are each independently (C2-C20) alkyl, (C1-C20) alkoxy, halo (C1-C20) alkyl, (C1-C20) alkylcarbonyl, (C1-C20) alkoxycarbonyl, (C6-C20) arylcarbonyl, tri(C1-C20) alkylsilyl, carboxyl, hydroxy, amino, nitro, cyano, or halogen;

$R_3$ is (C1-C20) alkyl, (C1-C20) alkoxy, halo (C1-C20) alkyl, (C1-C20) alkylcarbonyl, (C1-C20) alkoxycarbonyl, (C6-C20) arylcarbonyl, tri(C1-C20) alkylsilyl, carboxyl, hydroxy, amino, nitro, cyano, or halogen;

$R^a$ is hydrogen, (C1-C20) alkyl, or (C6-C20) aryl;

a and b are each independently an integer of 1 to 4;

c is an integer of 0 to 4;

when a, b, and c are integers of 2 or more, $R_1$, $R_2$, and $R_3$ may be the same as or different from each other; and p is an integer of 1 to 3.

As an example, in Chemical Formula 1, when p is an integer of 2 or more, $R^a$, $R_3$, and c may be the same as or different from each other.

Since the diamine according to an exemplary embodiment has the structural characteristics described above, for example, a biphenyl group structure, an asymmetric structure, and an amide bond, when the diamine is used as a monomer, it is possible to produce a film having significantly improved mechanical properties while maintaining excellent optical properties such as a yellow index, a haze, and a transmittance.

According to an exemplary embodiment, p may be, for example, an integer of 1 or 2, and more specifically, the diamine may be represented by the following Chemical Formula 2 or 3:

[Chemical Formula 2]

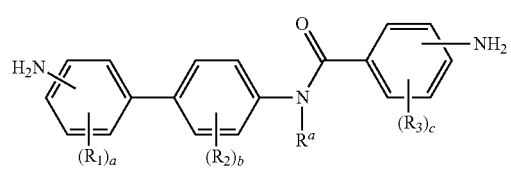

[Chemical Formula 3]

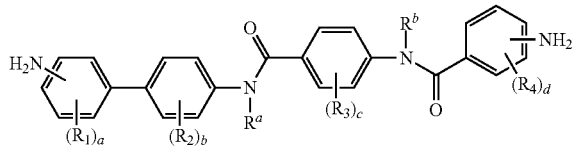

in Chemical Formulas 2 and 3, $R_1$ and $R_2$ are each independently (C2-C7) alkyl, (C1-C7) alkoxy, halo (C1-C7) alkyl, (C1-C7) alkylcarbonyl, (C1-C7) alkoxycarbonyl, (C6-C12) arylcarbonyl, tri (C1-C7) alkylsilyl, carboxyl, hydroxy, amino, nitro, cyano, or halogen;

$R_3$ and $R_4$ are each independently (C1-C7) alkyl, (C1-C7) alkoxy, halo (C1-C7) alkyl, (C1-C7) alkylcarbonyl, (C1-C7) alkoxycarbonyl, (C6-C12) arylcarbonyl, tri (C1-C7) alkylsilyl, carboxyl, hydroxy, amino, nitro, cyano, or halogen;

$R^a$ and $R^b$ are each independently hydrogen, (C1-C7) alkyl, or (C6-C12) aryl;

a and b are each independently an integer of 1 to 3;

c and d are each independently an integer of 0 to 3; and when a, b, c, and d are integers of 2 or more, $R_1$, $R_2$, $R_3$, and $R_4$ may be the same as or different from each other.

As an example, in Chemical Formulas 1 to 3, at least one of $R_1$ to $R_4$ may include an alkyl group substituted with fluoro, at least one of $R_1$ and $R_2$ may include an alkyl group substituted with fluoro, at least one of $R_1$'s may include an alkyl group substituted with fluoro, and at least one of $R_2$'s may include an alkyl group substituted with fluoro. Therefore, it is possible to further effectively prevent deterioration of the optical properties of the film. In this case, the alkyl group may be as described above, the alkyl group substituted with fluoro may be a perfluoroalkyl group, and more specifically, may be —$CF_3$, —$C_2F_5$, —$C_3F_7$, —$C_4F_9$, or $C_5F_{11}$, but is not limited thereto.

As an example, in Chemical Formulas 1 to 3, $R_1$ to $R_4$ may be the same as or different from each other, $R_1$, and $R_2$ and $R_3$ may be the same as or different from each other, $R_1$, and $R_2$ and $R_4$ may be the same as or different from each other, $R_1$ and $R_2$ may be the same as or different from each other, and $R_3$ and $R_4$ may be the same as or different from each other.

As an example, in Chemical Formulas 1 to 3, a and b may be each independently 1 or 2, or may be, for example, 1.

As an example, in Chemical Formulas 1 to 3, c and d may be each independently an integer of 0 to 2. For example, c may be an integer of 0 to 2, d may be 0 or 1, and c and d may be each independently 0 or 1.

As an example, in Chemical Formulas 1 to 3, a and b may be 1 or 2, c may be an integer of 0 to 2, and d may be 0 or 1, but the present invention is not limited thereto.

According to an exemplary embodiment, $R^a$ and $R^b$ may be each independently hydrogen or (C1-C7) alkyl, and may be, for example, hydrogen.

A fluoro-substituted alkyl group that may reduce a charge transfer complex (CTC) effect is introduced into the biphenyl group, such that it is possible to more effectively prevent deterioration of the optical properties of the film. In this case, the fluoro-substituted alkyl group may be as described above. More specifically, the diamine may be represented by the following Chemical Formula 4 or 5:

[Chemical Formula 4]

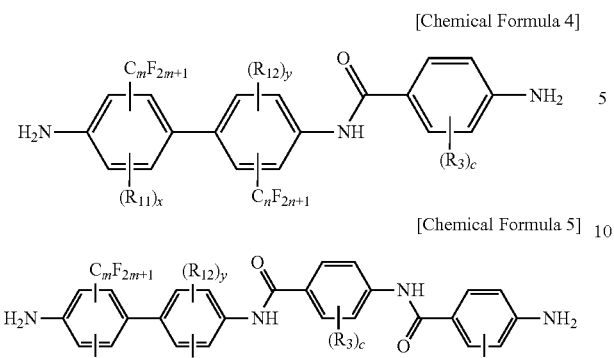

[Chemical Formula 5]

in Chemical Formulas 4 and 5, c and d may be as described above;

$R_3$ and $R_4$ are each independently (C1-C7) alkyl, (C1-C7) alkoxy, halo (C1-C7) alkyl, carboxyl, hydroxy, amino, or halogen;

$R_{11}$ and $R_{12}$ are each independently (C2-C7) alkyl, halo (C1-C7) alkyl, or halogen;

n and m are each independently an integer of 1 to 5;

x, y, c, and d are each independently an integer of 0 to 2; and when x, y, c, and d are 2, $R_{11}$, $R_{12}$, $R_3$, and $R_4$ may be the same as or different from each other.

In Chemical Formula 5, $R_3$ and $R_4$ may be the same as or different from each other.

In Chemical Formulas 4 and 5, $R_{11}$ and $R_{12}$ may be the same as or different from each other, and for example, $R_{11}$ and $R_{12}$ may be each independently (C2-C7) alkyl.

n and m may be each independently an integer of 1 to 3 or an integer of 1 or 2, and may be, for example, 1.

In addition, x and y may be the same as or different from each other. For example, x and y may be each independently 0 or 1, or x and y may be 0, but are not limited thereto.

More specifically, the fluoro-substituted alkyl group may be substituted at the ortho position of the biphenyl group. While not wishing to be bound by a certain theory, the fluoro-substituted alkyl group is substituted at the ortho position of the biphenyl group, such that it is possible to induce a twisted structure of two aryl groups in biphenyl, and to reduce a packing density and the CTC effect in the polyimide structure or between the chains due to a steric hindrance effect. Therefore, the optical properties of the polyimide-based film, for example, the yellow index and the haze, may be further improved.

Specifically, the diamine may be represented by the following Chemical Formula 6 or 7:

[Chemical Formula 6]

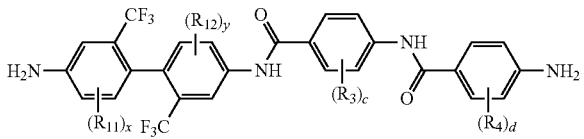

[Chemical Formula 7]

in Chemical Formulas 6 and 7, x, y, c, and d may be as described above;

$R_3$ and $R_4$ are each independently (C1-C5) alkyl, (C1-C5) alkoxy, halo (C1-C5) alkyl, carboxyl, hydroxy, amino, or halogen;

$R_{11}$ and $R_{12}$ are each independently (C2-C5) alkyl, halo (C1-C5) alkyl, or halogen; and when x, y, c, and d are 2, $R_{11}$, $R_{12}$, $R_3$, and $R_4$ may be the same as or different from each other.

In Chemical Formula 7, $R_3$ and $R_4$ may be the same as or different from each other.

In addition, in Chemical Formulas 6 and 7, x and y may be 0 or 1, $R_{11}$ and $R_{12}$ may be the same as or different from each other, and for example, $R_{11}$ and $R_{12}$ may be each independently (C2-C5) alkyl.

The diamine according to an exemplary embodiment may be, for example, selected from the following compounds, but is not limited thereto:

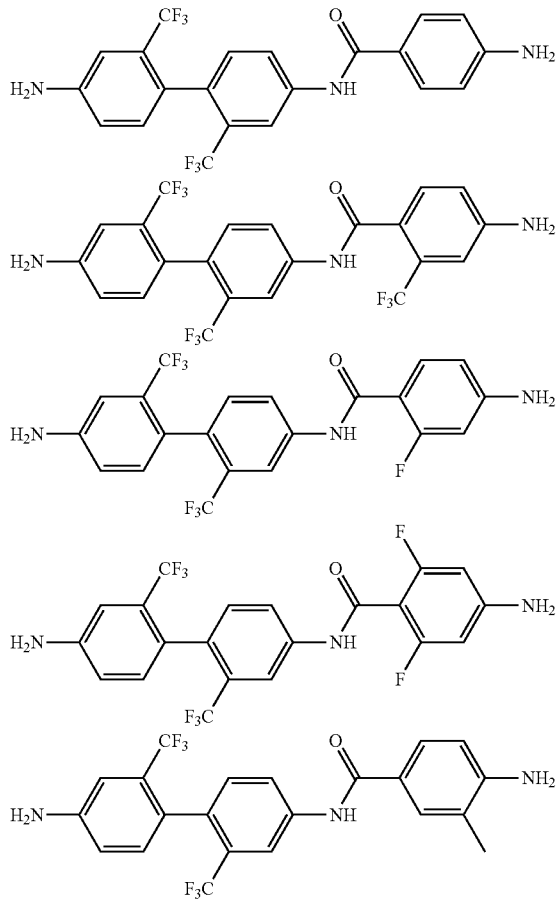

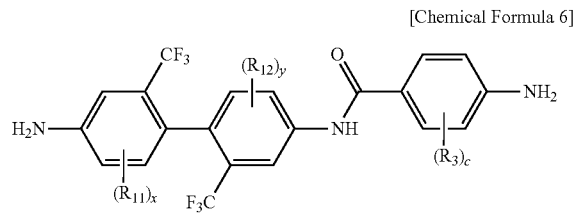

-continued

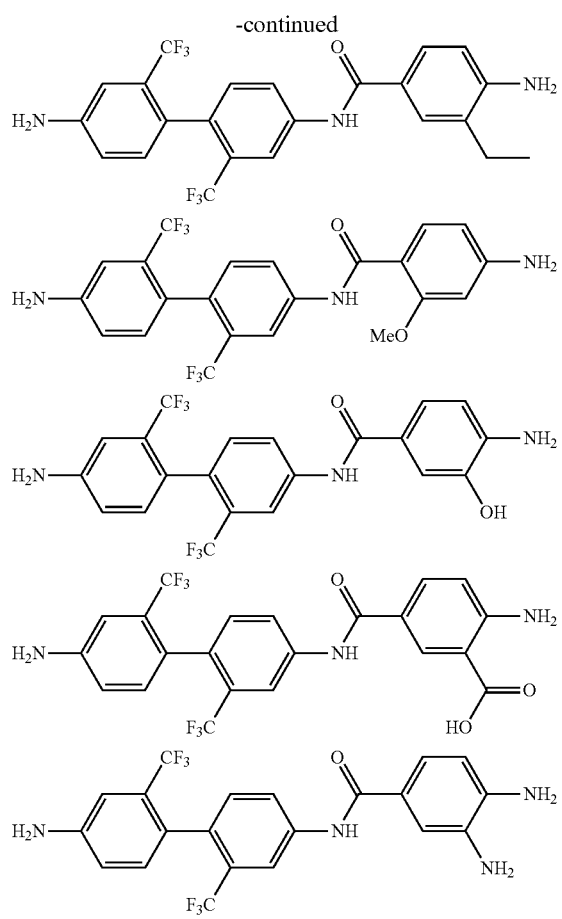

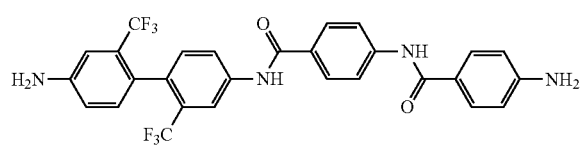

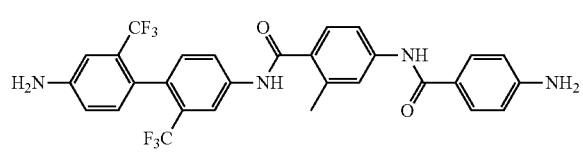

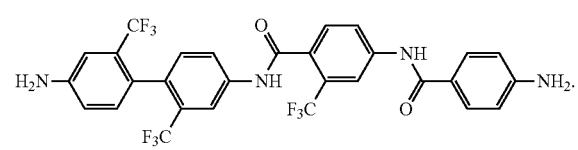

In addition, another exemplary embodiment provides a method of preparing a diamine.

The method of preparing a diamine according to an exemplary embodiment may include preparing a diamine represented by the following Chemical Formula 1 by reducing a compound represented by the following Chemical Formula A under a reduction catalyst:

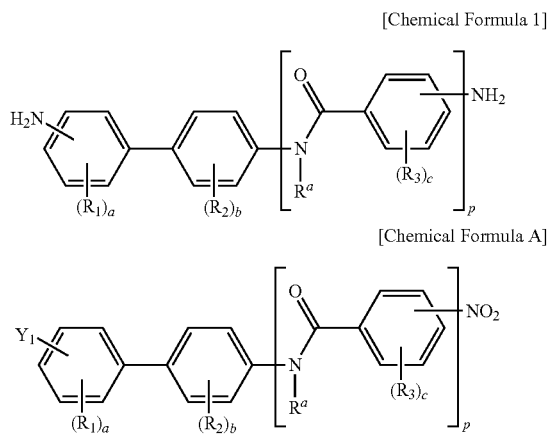

in Chemical Formulas 1 and A,

Y$_1$ is nitro or amino; and the definitions of R$_1$ to R$_3$, R$^a$, a, b, c, and p are the same as those in Chemical Formula 1.

According to an exemplary embodiment, the reduction catalyst may be selected from Zn, Cu, Ag, Au, Cd, Hg, Fe, K$_4$[Fe(CN)$_6$], NaBH$_4$, and a combination thereof. In addition, the reduction catalyst may further include a cocatalyst selected from NH$_4$C$_1$, H$_2$CO$_3$, H$_3$PO$_4$, HCl, CH$_3$COOH, and a combination thereof, and specifically, the reduction reaction may be performed using Fe and NH$_4$Cl together.

In addition, the reduction reaction may be performed at 40 to 80° C. for 1 to 30 hours, and specifically, may be performed at 50 to 70° C. for 10 to 30 hours.

According to an exemplary embodiment, the compound represented by Chemical Formula A may be prepared by reacting Y$_2$ of a compound represented by the following Chemical Formula A-1 with X of a compound represented by the following Chemical Formula A-2:

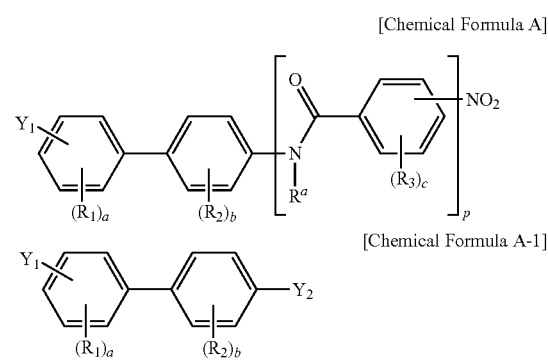

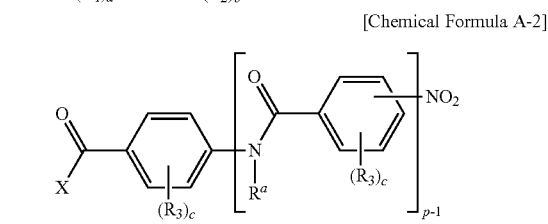

in Chemical Formulas A, A-1, and A-2, x is halogen;

Y$_1$ is nitro or amino;

$Y_2$ is

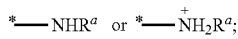

and the definitions of $R_1$ to $R_3$, $R^a$, a, b, c, and p are the same as those in Chemical Formula 1.

The reaction according to an exemplary embodiment may be performed at 20 to 40° C. for 1 to 10 hours, and specifically, may be performed at 20 to 30° C. for 1 to 5 hours.

In addition, still another exemplary embodiment provides a polymer produced using the diamine as a monomer.

Specifically, the polymer according to an exemplary embodiment may have a structural unit derived from the diamine; and a structural unit derived from a dianhydride, a structural unit derived from an aromatic diacid dichloride, or a combination thereof.

The polymer may be, for example, a polyamic acid-based polymer and/or a polyimide-based polymer having an amic acid moiety and/or an imide moiety by having a structural unit derived from the diamine represented by Chemical Formula 1 and a structural unit derived from the dianhydride that are adjacent to each other; a polyamide-based polymer having an amide moiety by having a structural unit derived from the diamine represented by Chemical Formula 1 and a structural unit derived from the aromatic diacid dichloride that are adjacent to each other; or a polyamic acid amide-based polymer and/or a polyamideimide-based polymer by having a structural unit derived from the diamine represented by Chemical Formula 1 and a structural unit derived from the dianhydride that are adjacent to each other and having a structural unit derived from the diamine represented by Chemical Formula 1 and a structural unit derived from the aromatic diacid dichloride that are adjacent to each other.

The polymer according to an exemplary embodiment may further have a structural unit derived from a known diamine, in addition to the structural unit derived from the diamine represented by Chemical Formula 1.

The known diamine is not particularly limited, and for example, one or two or more selected from p-phenylenediamine (p-PDA), m-phenylenediamine (m-PDA), 4,4'-oxydianiline (4,4'-ODA), 3,4'-oxydianiline (3,4'-ODA), 2,2-bis[4-(4-aminophenoxy)phenyl]propane (BAPP), 1,4-bis(4-aminophenoxy)benzene (TPE-Q), 1,3-bis(4-aminophenoxy)benzene (TPE-R), 4,4'-bis(4-aminophenoxy)biphenyl (BAPB), bis[4-(4-aminophenoxy)phenyl]sulfone (BAPS), bis[4-(3-aminophenoxy)phenyl]sulfone (m-BAPS), 3,3'-dihydroxy-4,4'-diaminobiphenyl (HAB), 3,3'-dimethylbenzidine (TB), 2,2'-dimethylbenzidine (m-TB), 2,2'-bis(trifluoromethyl)benzidine (TFMB), 1,4-bis(4-amino-2-trifluoromethylphenoxy)benzene (6FAPB), 2,2'-bis(trifluoromethyl)-4,4'-diaminodiphenyl ether (6FODA), 1,3-bis(3-aminophenoxy)benzene (APB), 1,4-naphthalenediamine (1,4-ND), 1,5-naphthalenediamine (1,5-ND), 4,4'-diaminobenzanilide (DABA), 6-amino-2-(4-aminophenyl)benzoxazole, and 5-amino-2-(4-aminophenyl)benzoxazole may be used, but the known diamine is not limited thereto. Specifically, the diamine may be a fluorine-based aromatic diamine into which a fluorine substituent is introduced, and may be, for example, selected from 2,2'-bis(trifluoromethyl)benzidine (TFMB), 1,4-bis(4-amino-2-trifluoromethylphenoxy)benzene (6FAPB), 2,2'-bis(trifluoromethyl)-4,4'-diaminodiphenyl ether (6FODA), and a combination thereof. More specifically, 2,2'-bis(trifluoromethyl)benzidine (TFMB) may be used as the diamine.

As the fluorine-based aromatic diamine compound is additionally used, the charge transfer effect is suppressed due to the fluorine substituent, and thus it is possible to impart more excellent optical properties to the film. In addition, the mechanical strength of the film may be further improved.

Specifically, in a case where the diamine of Chemical Formula 1 and the known diamine are used together, the diamine of Chemical Formula 1 and the known diamine may be used at a molar ratio of 1:1 to 1:100, specifically, at a molar ratio of 1:1 to 1:80, and more specifically, at a molar ratio of 1:1 to 1:50, but the molar ratio is not limited thereto. When the molar ratio satisfies the above range, the mechanical properties of the film may be more excellent.

The dianhydride according to an exemplary embodiment may be any compound having an acid dianhydride functional group, and may be, for example, an aromatic dianhydride, an alicyclic dianhydride, or a combination thereof. As the aromatic dianhydride, for example, one or two or more selected from 9,9-bis(3,4-dicarboxyphenyl)fluorene dianhydride (BPAF), 4,4'-(hexafluoroisopropylidene)diphthalic anhydride (6FDA), biphenyltetracarboxylic dianhydride (BPDA), oxydiphthalic dianhydride (ODPA), sulfonyl diphthalic anhydride ($SO_2DPA$), isopropylidenediphenoxy bis(phthalic anhydride) (6HDBA), 4-(2,5-dioxotetrahydrofuran-3-yl)-1,2,3,4-tetrahydronaphthalene-1,2-dicarboxylic dianhydride (TDA), 1,2,4,5-benzene tetracarboxylic dianhydride (PMDA), and benzophenone tetracarboxylic dianhydride (BTDA) may be used, but the aromatic dianhydride is not limited thereto. Specifically, the aromatic dianhydride may be 9,9-bis(3,4-dicarboxyphenyl)fluorene dianhydride (BPAF), 4,4'-(hexafluoroisopropylidene)diphthalic anhydride (6FDA), or a combination thereof. More specifically, a fluorine-based aromatic dianhydride compound may be used, and for example, 4,4'-(hexafluoroisopropylidene)diphthalic anhydride (6FDA) may be used. By using the aromatic dianhydride, mechanical strength, in particular, a modulus of the film may be more effectively improved as well as optical properties of the film.

As the alicyclic dianhydride, for example, one or two or more selected from the group consisting of 1,2,3,4-cyclobutanetetracarboxylic dianhydride (CBDA), 5-(2,5-dioxotetrahydrofuryl)-3-methylcyclohexene-1,2-dicarboxylic dianhydride (DOCDA), bicyclo[2.2.2]oct-7-ene-2,3,5,6-tetracarboxylic dianhydride (BTA), bicyclooctene-2,3,5,6-tetracarboxylic dianhydride (BODA), 1,2,3,4-cyclopentanetetracarboxylic dianhydride (CPDA), 1,2,4,5-cyclohexanetetracarboxylic dianhydride (CHDA), 1,2,4-tricarboxy-3-methylcarboxycyclopentane dianhydride (TMDA), 1,2,3,4-tetracarboxycyclopentane dianhydride (TCDA), and derivatives thereof may be used, but the alicyclic dianhydride is not limited thereto. Specifically, the alicyclic dianhydride may be 1,2,3,4-cyclobutanetetracarboxylic dianhydride (CBDA).

More specifically, as the dianhydride according to an exemplary embodiment, a combination of an aromatic dianhydride and an alicyclic dianhydride may be used, a combination of a fluorine-based aromatic dianhydride and an alicyclic dianhydride may be used, or a combination of 4,4'-(hexafluoroisopropylidene)diphthalic anhydride (6FDA) and 1,2,3,4-cyclobutanetetracarboxylic dianhydride (CBDA) may be used.

In addition, when the polymer according to an exemplary embodiment is produced, an equivalent ratio of a diamine to a dianhydride, an aromatic diacid dichloride, or a combination thereof is not particularly limited, and may be 1:0.9 to 1.1, and specifically, 1:0.9 to 1:1. When the equivalent ratio satisfies the above range, the physical properties of the film including film forming properties may be further improved.

The aromatic diacid dichloride reacts with the diamine described above to form an amide structure in the polymer chain, such that the mechanical properties of the film including a modulus may be further improved in a range in which the optical properties of the film are not deteriorated.

As the aromatic diacid dichloride, one or two or more selected from the group consisting of isophthaloyl dichloride (IPC), terephthaloyl dichloride (TPC), 1,1'-biphenyl-4,4'-dicarbonyl dichloride (BPC), 1,4-naphthalenedicarboxylic dichloride (NPC), 2,6-naphthalenedicarboxylic dichloride (NTC), 1,5-naphthalenedicarboxylic dichloride (NEC), and derivatives thereof may be used. For example, TPC may be used, but the aromatic diacid dichloride is not limited thereto.

In an exemplary embodiment, in a case where the polymer has a structural unit derived from the aromatic diacid dichloride, a content of the aromatic diacid dichloride is not particularly limited, and the aromatic diacid dichloride may be contained in an amount of 50 mol or less or 50 mol or more with respect to 100 mol of the diamine. Even when the aromatic diacid dichloride is contained in an amount of 50 mol or more with respect to 100 mol of the diamine, as the aromatic diacid dichloride is combined with the diamine of Chemical Formula 1, the mechanical properties of the film may be further improved while maintaining excellent optical properties of the film.

In addition, still another exemplary embodiment provides a composition containing the polymer described above.

Specifically, the composition according to an exemplary embodiment may be a composition for forming a film containing the polymer and an organic solvent.

The composition according to an exemplary embodiment contains the polymer described above, such that it is possible to provide a film having significantly improved optical and mechanical properties, and specifically, a polyimide-based film including polyimide, polyamide, or a combination thereof. In this case, a combination of polyimide and polyamide may mean a polyamideimide or a mixture of polyimide and polyamide. In particular, the composition according to an exemplary embodiment may provide a film having high transparency, a low yellow index value, and a significantly improved modulus value.

The organic solvent contained in the composition according to an exemplary embodiment may be one or a mixture of two or more selected from ketones such as γ-butyrolactone, 1,3-dimethyl-2-imidazolidinone, methyl ethyl ketone, cyclohexanone, cyclopentanone, and 4-hydroxy-4-methyl-2-pentanone; aromatic hydrocarbons such as toluene, xylene, and tetramethylbenzene; glycol ethers (cellosolves) such as ethylene glycol monoethyl ether, ethylene glycol monomethyl ether, ethylene glycol monobutyl ether, diethylene glycol monoethyl ether, diethylene glycol monomethyl ether, diethylene glycol monobutyl ether, propylene glycol monomethyl ether, propylene glycol monoethyl ether, dipropylene glycol diethyl ether, and triethylene glycol monoethyl ether; acetates such as ethyl acetate, butyl acetate, ethylene glycol monoethyl ether acetate, ethylene glycol monobutyl ether acetate, diethylene glycol monoethyl ether acetate, and dipropylene glycol monomethyl ether acetate; alcohols such as methanol, ethanol, propanol, ethylene glycol, propylene glycol, and carbitol; and amides such as N,N-dimethylpropionamide (DMPA), N,N-diethylpropionamide (DEPA), N,N-dimethylacetamide (DMAc), N,N-diethylacetamide (DEAc), N,N-dimethylformamide (DMF), N,N-diethylformamide (DEF), N-methylpyrrolidone (NMP), N-ethylpyrrolidone (NEP), and N,N-dimethylmethoxy acetamide.

Specifically, the organic solvent may be one or a mixture of two or more selected from the amides described above. As an example, the organic solvent may be amides having a boiling point of 300° C. or lower, and specifically, may be N,N-diethylformamide (DEF), N,N-diethylacetamide (DEAc), N-ethylpyrrolidone (NEP), N,N-diethylpropionamide (DMPA), N,N-diethylpropionamide (DEPA), or a combination thereof.

In the composition for forming a film according to an exemplary embodiment, a solid content may be 5 to 20 wt %, 10 to 20 wt %, or 10 to 15 wt %, with respect to the total weight of the composition.

Hereinafter, a method of preparing a composition for forming a film according to an exemplary embodiment will be described in detail.

The method of preparing a composition for forming a film according to an exemplary embodiment may include: a step (A) of preparing a polyamic acid solution by dissolving a diamine compound in an organic solvent and then reacting a dianhydride; and a step (B) of preparing a composition for forming a film by adjusting a solid content.

Specifically, in the step (A), the diamine and the dianhydride are mixed at an equivalent ratio of 1:0.9 to 1:1.1 to polymerize a polyimide precursor. At this time, the polymerization conditions are not particularly limited, and the polymerization reaction may be performed in an inert gas atmosphere, and for example, may be performed while nitrogen or argon gas is refluxed in a reactor. In addition, the reaction temperature may be 20° C. to 70° C. or 30° C. to 70° C., and the reaction time may be 5 hours to 30 hours or 5 hours to 20 hours, but the reaction temperature and the reaction time are not limited thereto.

In addition, the step (A) may further include a step of adding an aromatic diacid dichloride. In this case, the polymerization may be performed by adding the diamine, the dianhydride, and the aromatic diacid dichloride at the same time, or the composition may be prepared by preparing an oligomer having an amine terminus by reacting the diamine with the aromatic diacid dichloride and then reacting the oligomer with an additional diamine and dianhydride, but the present invention is not limited thereto. In the case where an oligomer having an amine terminus is prepared and then the oligomer is reacted with an additional diamine and dianhydride, block polyamideimide may be prepared, and the mechanical properties of the film may be further improved.

Specifically, in the case where an oligomer having an amine terminus is prepared, the step (A) may include: a step (i) of reacting a diamine with an aromatic diacid dichloride; a step (ii) of purifying and drying the obtained oligomer; and a step (iii) of preparing a polyamic acid solution by reacting the purified oligomer with a diamine and a dianhydride. In this case, the diamine may be added at a molar ratio of 1.01 to 2 relative to the aromatic diacid dichloride to prepare an amine-terminated polyamide oligomer. A molecular weight of the oligomer is not particularly limited, and for example, a weight average molecular weight of the oligomer may be 1,000 to 3,000 g/mol.

In addition, the step (A) may further include a step of preparing a polyamic acid solution and then imidizing the polyimide precursor to obtain a polyimide-based resin. In this case, the imidization may be performed by chemical imidization, and the imidization may be performed by further including one or two or more selected from an imidization catalyst and a dehydrating agent. One or two or more selected from pyridine, isoquinoline, and β-quinoline may be used as the imidization catalyst. In addition, one or two or more selected from acetic anhydride, phthalic anhydride, and maleic anhydride may be used as the dehydrating agent, but the present invention is not limited thereto. In this case, the imidization of the polyimide precursor may be performed, the imidized polyimide precursor may be precipitated in a solvent and purified to obtain a solid (polyimide powder), and the solid may be dissolved in an organic solvent so that a solid content is adjusted, thereby obtaining a composition for forming a polyimide film.

In a case where the chemical imidization is not performed in an exemplary embodiment, the composition for forming a film according to an exemplary embodiment may contain polyimide and/or polyamic acid, and an organic solvent.

In addition, still another exemplary embodiment of the present invention provides a film produced using the composition for forming a film. Specifically, the film may be a polyimide-based film including polyimide, polyamide, or a combination thereof.

The film according to an exemplary embodiment may have a low yellow index, excellent transparency, a high modulus, and excellent mechanical strength.

A thickness of the polyimide film according to an exemplary embodiment may be 1 to 500 um, 20 to 500 um, 30 to 300 um, or 40 to 100 um.

A yellow index (YI) of the film according to an exemplary embodiment may be 20 or less, 15 or less, 10 or less, 7 or less, or 5 or less, when measured according to ASTM E313.

A haze of the film according to an exemplary embodiment may be 2.0% or less, 1.5% or less, or 1.0% or less, when measured according to ASTM D1003.

A total light transmittance of the film according to an exemplary embodiment may be 80% or more, 85% or more, or 87% or more, when measured according to ASTM D1003.

A modulus of the film according to an exemplary embodiment may be 5 GPa or ore, 5.5 GPa or more, 6 GPa or more, 7 GPa or more, 7.3 GPa or more, or 7.5 GPa or more, when measured according to ASTM D882.

The film according to an exemplary embodiment may have a YI of 10 or less when measured according to ASTM E313, a haze of 2.0% or less when measured according to ASTM D1003, a total light transmittance of 80% or more when measured according to ASTM D1003, and a modulus of 5 GPa or more when measured according to ASTM D882. Specifically, the film according to an exemplary embodiment may have a YI of 15 or less, a haze of 1.5% or less, a total light transmittance of 85% or more, and a modulus of 6 GPa or more. More specifically, the film according to an exemplary embodiment may have a YI of 10 or less, a haze of 1.0% or less, a total light transmittance of 87% or more, and a modulus of 7 GPa or more.

The film according to an exemplary embodiment is produced using a diamine compound into which a trifluoromethyl group, which is a specific functional group, is introduced at a specific skeleton and at a specific position, such that excellent optical properties and mechanical properties may be implemented as described above. Specifically, the film according to an exemplary embodiment includes a structural unit derived from the diamine represented by Chemical Formula 1, such that it is possible to provide a film excellent in all of optical properties, mechanical strength, and flexibility. Therefore, the film according to an exemplary embodiment may be applied to various fields such as a device substrate, a display cover substrate, an optical film, an integrated circuit (IC) package, an adhesive film, a multi-layer flexible printed circuit (FPC), a tape, a touch panel, and an optical disk protective film.

Hereinafter, a method of producing a film according to an exemplary embodiment of the present invention will be described in detail.

The film according to an exemplary embodiment may be produced by applying a composition containing the polymer according to an exemplary embodiment and a solvent to a substrate, and performing drying and/or stretching.

Specifically, the film according to an exemplary embodiment may be produced by chemical curing or thermal curing.

The chemical curing may include: preparing a polyimide-based resin by imidizing the polyamic acid solution according to an exemplary embodiment; and forming a film by applying a resin composition (composition for forming a film) in which the polyimide-based resin is dissolved in an organic solvent.

The imidization is the same as described above and thus will be omitted.

The forming of the film is a step of applying a composition for forming a film to a substrate and then forming a film by performing drying through a heat treatment. For example, glass, stainless steel, a film, or the like may be used as the substrate, and the application may be performed by a die coater, an air knife, a reverse roll, spray, a blade, casting, gravure, spin coating, or the like.

The heat treatment may be performed, for example, in stages. For example, a stepwise heat treatment may be performed by performing primary drying at 70° C. to 160° C. for 1 minute to 2 hours and performing secondary drying at 150° C. to 350° C. for 1 minute to 2 hours. However, the heat treatment is not limited to the temperature and time conditions, and for example, the primary drying may be performed at 80° C. to 150° C., 70° C. to 110° C., 130° C. to 150° C., 90° C., 120° C., or 140° C. for 10 minutes to 90 minutes, 10 minutes to 60 minutes, 20 minutes to 50 minutes, or 30 minutes, and the secondary drying may be performed at 200° C. to 300° C., 220° C. to 300° C., or 250° C. to 300° C. for 10 minutes to 90 minutes, 30 minutes to 90 minutes, or 40 minutes to 80 minutes. In this case, in the stepwise heat treatment, the temperature may be preferably raised in a range of 1 to 20° C./min during each step movement. In addition, the heat treatment may be performed in a separate vacuum oven, an oven filled with an inert gas, or the like, but is not limited thereto.

In addition, according to an exemplary embodiment, the thermal curing may be performed at 100 to 450° C., 120 to 450° C., or 150 to 450° C. More specifically, the thermal curing may be performed at 80 to 100° C. for 1 minute to 2 hours, at higher than 100 to 200° C. for 1 minute to 20 hours, or at higher than 200 to 450° C. for 1 minute to 2 hours, and stepwise thermal curing may be performed under two or more temperature conditions selected therefrom. In addition, the thermal curing may be performed in a separate vacuum oven, an oven filled with an inert gas, or the like, but is not limited thereto. In addition, before the thermal curing, drying may be additionally performed, if necessary. The drying may be performed at 50° C. to 150° C., 50° C. to 130° C., 60° C. to 100° C., or about 80° C., but is not limited to the above range.

In addition, one or two or more additives selected from a flame retardant, an adhesion enhancer, inorganic particles, an antioxidant, an ultraviolet inhibitor, and a plasticizer may be further mixed with the polyamic acid solution.

In addition, the film according to an exemplary embodiment may be provided as a multi-layer structure including two or more layers.

Specifically, the multi-layer structure may further include a functional coating layer formed on at least one other surface of the film or the substrate, if necessary. Non-limiting examples of the functional coating layer include a hard coating layer, an anti-static layer, an anti-fingerprint layer, an anti-fouling layer, an anti-scratch layer, a low refractive layer, an anti-reflective layer, and an impact absorption layer, and one or two or more functional layers may be provided.

In addition, in an exemplary embodiment, various types of molded articles may be manufactured using the film. Examples of the molded article include, but are not limited to, a printed wiring board and flexible circuit board including a film, a protective film, or an insulating film. Specifically, the film according to an exemplary embodiment may be applied to a protective film that may replace cover glass, and may be widely used in various industrial fields including a display device.

More specifically, the film according to an exemplary embodiment may be used as a window cover film of a flexible display device or the like.

The film according to an exemplary embodiment includes a structural unit derived from the diamine represented by Chemical Formula 1, such that excellent optical properties such as high transparency and a low yellow index and an excellent modulus may be implemented. Therefore, the film according to an exemplary embodiment may be used as a window cover film of a flexible display panel or the like. The window cover film including the film according to an exemplary embodiment may be used as an alternative material for tempered glass because it has excellent visibility due to its more excellent optical properties, a high modulus, and excellent mechanical strength.

Hereinafter, the present invention will be described in detail with reference to one exemplary embodiment, but the present invention is not limited to the following exemplary embodiment.

In the following experiment, physical properties were measured as follows.

<Yellow Index (YI)>

A yellow index was measured in accordance with ASTM E313 standard using a spectrophotometer (COH-5500, manufactured by Nippon Denshoku Industries Co., Ltd.), and the measurement results were evaluated according to the following criteria.

O: Yellow index of less than 5, X: Yellow index of 5 or more

<Total Light Transmittance>

A total light transmittance (%) of a polyimide film was measured in the entire 400 nm to 700 nm wavelength region using a light transmittance meter (COH-5500, manufactured by Nippon Denshoku Industries Co., Ltd.) according to ASTM D1003 standard.

<Haze>

In order to measure transparency of the polyimide film, a value of a haze (%) was measured using a spectrophotometer (COH-5500, manufactured by Nippon Denshoku Industries Co., Ltd.) according to ASTM D1003 standard.

<Modulus>

A modulus (GPa) of a polyimide film having a length of 50 mm and a width of 10 mm was measured under a condition in which the film was pulled at 25° C. and 50 mm/min using UTM 3365 manufactured by Instron Corporation according to ASTM D882 standard.

<Weight Average Molecular Weight>

A weight average molecular weight was measured by dissolving a film in a DMAc eluent containing 0.05 M LiCl. Waters GPC system, Waters 1515 isocratic HPLC Pump, and Waters 2414 Refractive Index detector were used for GPC, Olexis, Polypore, and a mixed D column were connected to each other and used as a column, polymethyl methacrylate (PMMA STD) was used as a standard material, and the analysis was performed at 35° C. and a flow rate of 1 mL/min.

[Example 1] Preparation of Diamine 1

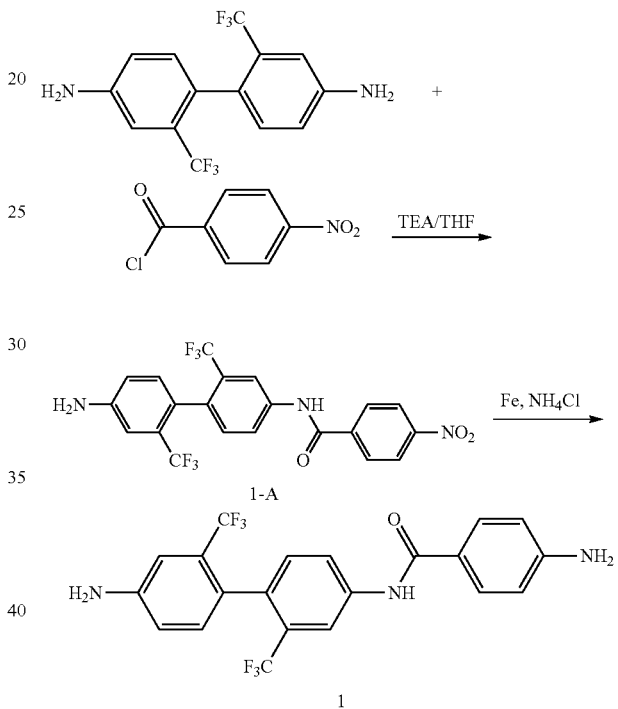

Preparation of Compound 1-A

In a nitrogen environment, 15.0 g of 2,2'-bis(trifluoromethyl)benzidine (TFMB), 50.0 ml of tetrahydrofuran (THF), and 9.79 ml of triethylamine (TEA) were added, and the solution was cooled to 0° C. A solution in which 8.69 g of 4-nitrobenzoyl chloride was dissolved in 50.0 ml of another THF was prepared, and the solution was added dropwise to the TFMB solution in a nitrogen environment for 2 hours. After completion of the dropwise addition, the mixture was additionally stirred at room temperature (25° C.) for 2 hours, and then 100 ml of a $Na_2CO_3$ solution was added. Thereafter, washing was performed using ethyl acetate and distilled water, and then the solvent was removed by distillation under reduced pressure, thereby obtaining a yellow solid compound 1-A (20.6 g).

Preparation of Diamine 1

To 20.6 g of the compound 1-A prepared above, 15.0 g of ammonium chloride ($NH_4Cl$) and 15.7 g of an Fe powder were added, and 160 ml of tetrahydrofuran (THF), 80 ml of methanol (MeOH), and 80 ml of distilled water were added. The mixture was reacted at 60° C. for 20 hours while being stirred vigorously, and then a residual Fe powder was removed by filtration through a celite pad. Thereafter, extraction was performed using ethyl acetate and distilled water, the solvent was removed by purification under reduced pressure, and then purification was performed by a column, thereby obtaining a diamine compound 1 (10.8 g, 53%).

$^1$H-NMR (DMSO-$d_6$, 500 MHz, ppm): 10.19 (s, 1H), 8.26 (d, 1H, J=2.0 Hz), 7.99 (dd, 1H, J=8.5, 2.0 Hz), 7.74 (d, 2H, J=8.5 Hz), 7.22 (d, 1H, J=8.0 Hz), 6.94 (m, 2H), 6.78 (dd, 2H, J=8.5, 2.0 Hz), 6.62 (d, 1H, J=8.5 Hz), 5.81 (s, NH$_2$), 5.65 (s, NH$_2$)

[Example 2] Preparation of Diamine 2

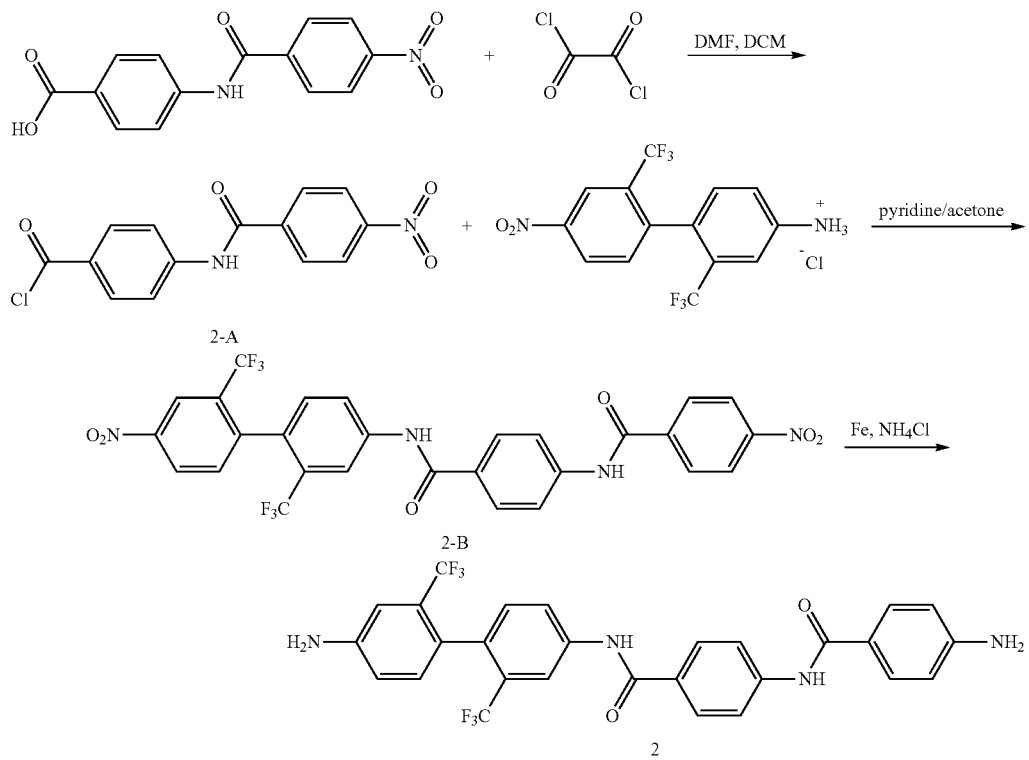

Preparation of Compound 2-A

In a nitrogen environment, 13 g of 4-[(4-nitrobenzoyl) amino]benzoic acid was dissolved in 260 ml of tetrahydrofuran (THF), and the solution was cooled to 0° C. To the solution, 8.7 g of oxalyl chloride was slowly added, 0.1 ml of dimethylformamide (DMF) was added, and then the mixture was stirred at room temperature (25° C.) for 6 hours. Thereafter, the solvent was removed by distillation under reduced pressure to obtain 13 g of 4-[(4-nitrobenzoyl) amino]benzoic chloride as a compound 2-A.

Preparation of Compound 2-B

In a nitrogen environment, 11.8 g of 4'-nitro-2,2'-bis (trifluoromethyl)[1,1'-biphenyl]-4-amine·HCl, 60 ml of acetone, and 8.4 g of pyridine were added. 11.1 g of the compound 2-A prepared above was dissolved in 150 ml of another acetone, and the mixture was added dropwise to the solution for 1 hour. After completion of the dropwise addition, the mixture was additionally stirred at room temperature (25° C.) for 2 hours, and then 200 ml of distilled water was added. Thereafter, washing was performed using ethyl acetate and distilled water, and then the solvent was removed by distillation under reduced pressure, thereby obtaining a white solid compound 2-B (18.3 g).

Preparation of Diamine 2

To 18.9 g of the compound 2-B prepared above, 15.8 g of ammonium chloride (NH$_4$Cl) and 16.5 g of an Fe powder were added, and 180 ml of tetrahydrofuran (THF), 90 ml of methanol (MeOH), and 90 ml of distilled water were added. The mixture was reacted at 60° C. for 20 hours while being stirred vigorously, and then a residual Fe powder was removed by filtration through a celite pad. Thereafter, extraction was performed using ethyl acetate and distilled water, the solvent was removed by purification under reduced pressure, and then purification was performed by a column, thereby obtaining a diamine 2 (11.2 g, 68%).

$^1$H-NMR (DMSO-$d_6$, 500 MHz, ppm): 10.44 (s, 1H), 10.05 (s, 1H), 8.29 (s, 1H), 8.04 (d, 1H, J=8.0 Hz), 8.00-7.94 (m, 4H), 7.76 (d, 2H, J=8.5 Hz), 7.28 (d, 1H, J=8.5 Hz), 6.96-6.95 (m, 2H), 6.79 (d, 1H, J=8.0 Hz), 6.63 (d, 2H, J=8.5 Hz), 5.82 (s, NH$_2$), 5.66 (s, NH$_2$)

[Example 3] Preparation of Diamine 3

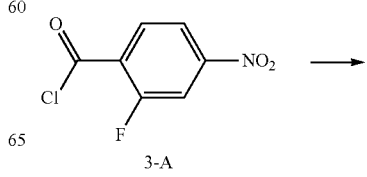

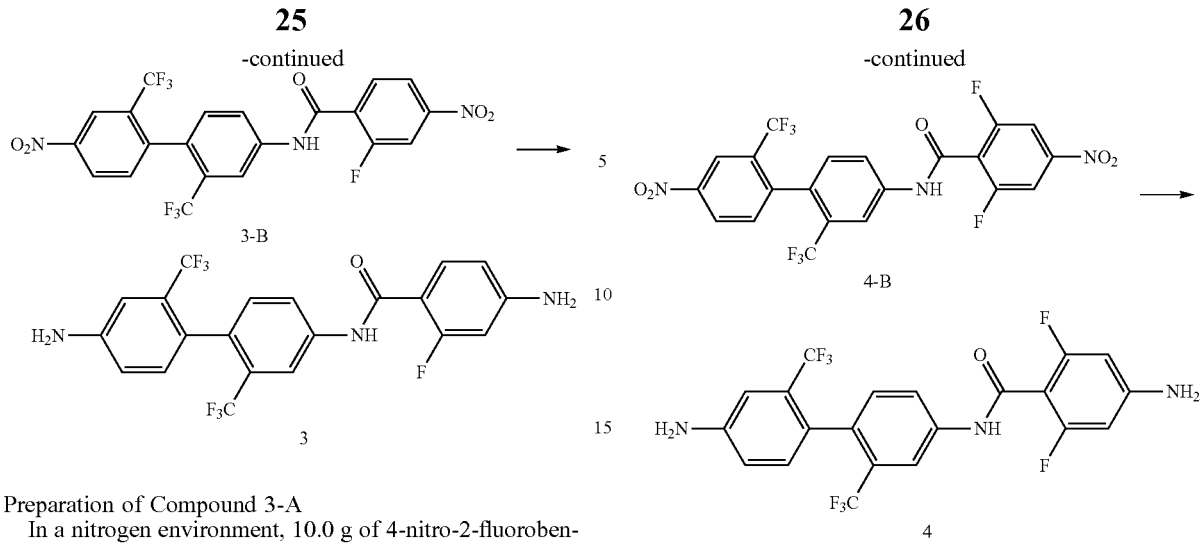

Preparation of Compound 3-A

In a nitrogen environment, 10.0 g of 4-nitro-2-fluorobenzoic acid was dissolved in 100 ml of dichloromethane (DCM), and then the solution was cooled to 0° C. To the solution, 12.3 g of oxalyl chloride was slowly added, 0.1 ml of dimethylformamide (DMF) was added, and then the mixture was stirred at room temperature (25° C.) for 6 hours. Thereafter, the solvent was removed by distillation under reduced pressure to obtain 11.2 g of 4-nitro-2-fluorobenzoylchloride as a compound 3-A.

Preparation of Compound 3-B

In a nitrogen environment, 22.7 g of 4'-nitro-2,2'-bis(trifluoromethyl)[1,1'-biphenyl]-4-amine·HCl, 120 ml of tetrahydrofuran (THF), and 16.2 g of pyridine were added. 11.2 g of the compound 3-A (4-nitro-2-fluorobenzoylchloride) was dissolved in 100 ml of another tetrahydrofuran (THF), and the mixture was added dropwise to the solution for 1 hour. After completion of the dropwise addition, the mixture was additionally stirred at room temperature (25° C.) for 2 hours, and then 200 ml of distilled water was added. Thereafter, washing was performed using ethyl acetate and distilled water, and then the solvent was removed by distillation under reduced pressure, thereby obtaining a white solid compound 3-B (28.8 g).

Preparation of Diamine 3

To 10.0 g of the compound 3-B prepared above, 8.3 g of ammonium chloride (NH$_4$Cl) and 8.6 g of an Fe powder were added, and 100 ml of tetrahydrofuran (THF), 50 ml of methanol (MeOH), and 50 ml of distilled water were added. The mixture was reacted at 60° C. for 20 hours while being stirred vigorously, and then a residual Fe powder was removed by filtration through a celite pad. Thereafter, extraction was performed using ethyl acetate and distilled water, the solvent was removed by purification under reduced pressure, and then purification was performed by a column, thereby obtaining a diamine 3 (7.5 g, 85%).

MS: m/z: M$^+$ calculated for $C_{21}H_{15}F_7N_3O^+$, 458.11, found 458.18

[Example 4] Preparation of Diamine 4

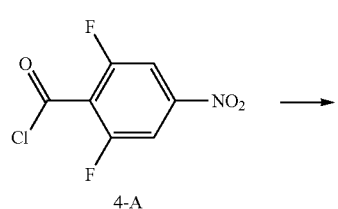

A diamine 4 (6.8 g, 77%) was obtained in the same manner as that of Example 3, except that 4-nitro-2,6-difluorobenzoic acid was used instead of 4-nitro-2-fluorobenzoic acid.

MS: m/z: M$^+$ calculated for $C_{21}H_{14}F_8N_3O^+$, 476.10, found 476.19

[Example 5] Preparation of Diamine 5

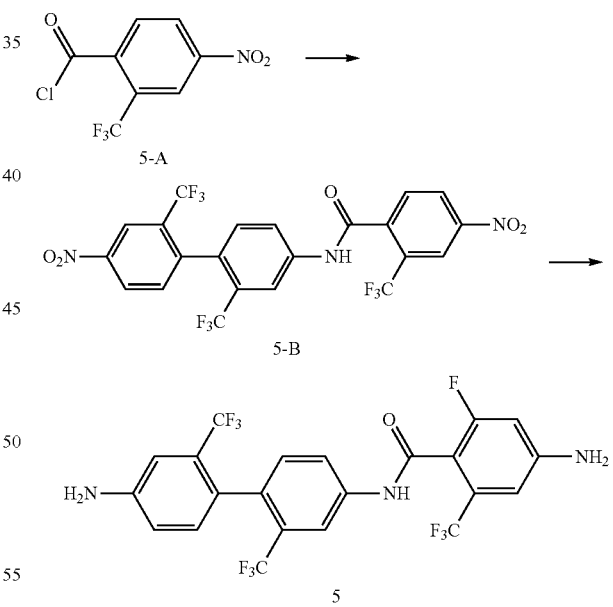

A diamine 5 (7.9 g, 88%) was obtained in the same manner as that of Example 3, except that 4-nitro-2-trifluoromethylbenzoic acid was used instead of 4-nitro-2-fluorobenzoic acid.

$^1$H-NMR (DMSO-d$_6$, 500 MHz, ppm): 10.55 (s, 1H), 8.15 (s, 1H), 7.81 (d, 1H, J=8.5 Hz), 7.38 (d, 1H, J=8.5 Hz), 7.19 (d, 1H, J=8.5 Hz), 6.90 (m, 3H), 6.77 (d, 1H, J=8.5 Hz), 6.72 (d, 1H, J=8.5 Hz), 5.95 (s, NH$_2$), 5.62 (s, NH$_2$)

[Example 6] Preparation of Diamine 6

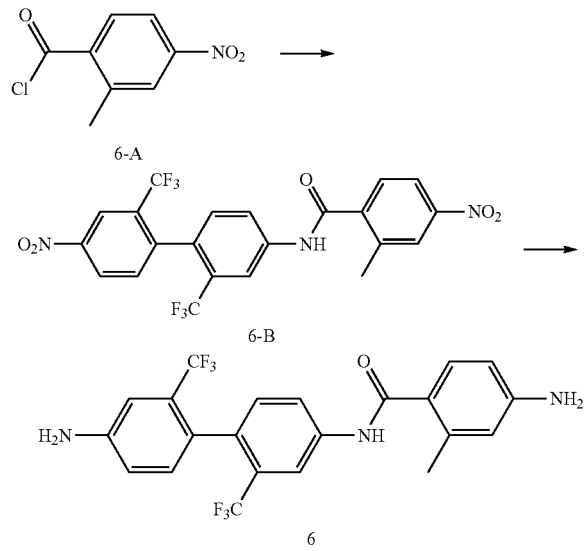

[Example 7] Preparation of Diamine 7

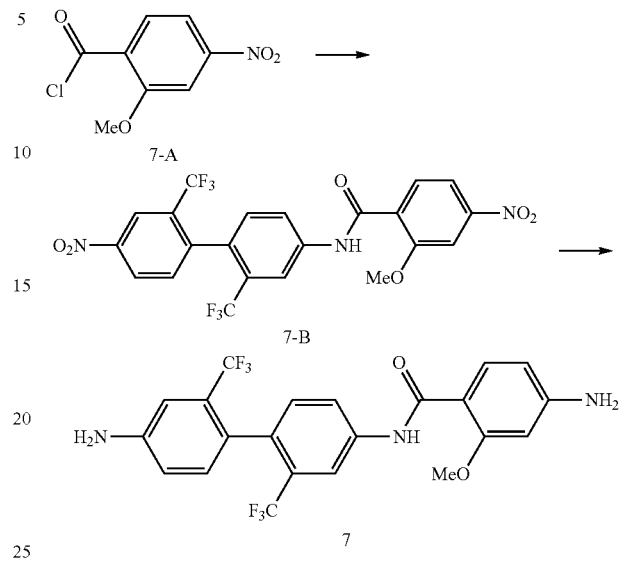

A diamine 6 (8.1 g, 92%) was obtained in the same manner as that of Example 3, except that 4-nitro-2-methyl-benzoic acid was used instead of 4-nitro-2-fluorobenzoic acid.

$^1$H-NMR (DMSO-$d_6$, 500 MHz, ppm): 10.09 (s, 1H), 8.25 (s, 1H), 8.01 (d, 1H, J=8.5 Hz), 7.64 (m, 2H), 7.23 (d, 1H, J=8.5 Hz), 6.94 (m, 2H), 6.66 (d, 1H, J=8.0 Hz), 5.66 (s, NH$_2$), 5.60 (s, NH$_2$), 3.35 (s, CH$_3$)

A diamine 7 (7.2 g, 81%) was obtained in the same manner as that of Example 3, except that 4-nitro methoxy-benzoic acid was used instead of 4-nitro-2-fluorobenzoic acid.

MS: m/z: M$^+$ calculated for $C_{22}H_{18}F_6N_3O_2^+$, 470.13, found 470.19

[Example 8] Preparation of Diamine 8

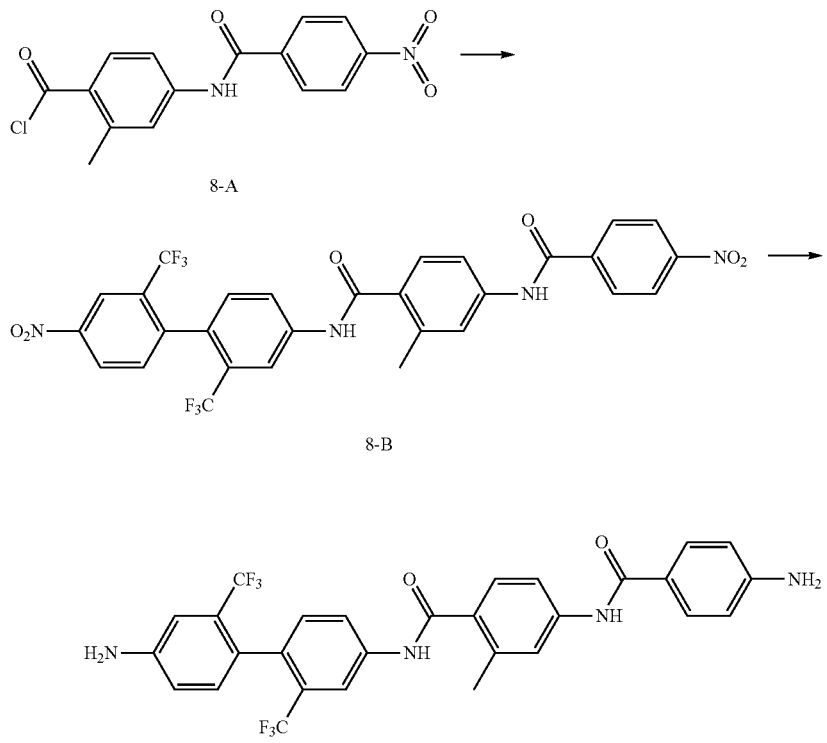

Preparation of Compound 8-A

In a nitrogen environment, 10.0 g of 4-[(4-nitrobenzoyl)amino]-2-methyl-benzoic acid was dissolved in 50 ml of tetrahydrofuran (THF) and 50 ml of dichloromethane (DCM), and the solution was cooled to 0° C. To the solution, 6.34 g of oxalyl chloride was slowly added, 0.1 ml of dimethylformamide (DMF) was added, and then the mixture was stirred at room temperature (25° C.) for 8 hours. Thereafter, the solvent was removed by distillation under reduced pressure to obtain 10.6 g of 4-[(4-nitrobenzoyl)amino]-2-methyl-benzoyl chloride as a compound 8-A.

Preparation of Compound 8-B

In a nitrogen environment, 11.7 g of 4'-nitro-2,2'-bis(trifluoromethyl)[1,1'-biphenyl]-4-amine·HCl, 60 ml of tetrahydrofuran (THF), and 8.4 g of pyridine were added. 10.6 g of 4-[(4-nitrobenzoyl)amino]-2-methyl-benzoyl chloride was dissolved in 50 ml of another tetrahydrofuran (THF), and the mixture was added dropwise to the solution for 1 hour. After completion of the dropwise addition, the mixture was additionally stirred at room temperature (25° C.) for 2 hours, and then 200 ml of distilled water was added. Thereafter, washing was performed using ethyl acetate and distilled water, and then the solvent was removed by distillation under reduced pressure, thereby obtaining a white solid compound 8-B (18.2 g).

Preparation of Diamine 8

To 10.0 g of the compound 8-B prepared above, 6.8 g of ammonium chloride (NH$_4$Cl) and 7.1 g of an Fe powder were added, and 100 ml of tetrahydrofuran (THF), 50 ml of methanol (MeOH), and 50 ml of distilled water were added. The mixture was reacted at 60° C. for 24 hours while being stirred vigorously, and then a residual Fe powder was removed by filtration through a celite pad. Thereafter, extraction was performed using ethyl acetate and distilled water, the solvent was removed by purification under reduced pressure, and then purification was performed by a column, thereby obtaining a diamine compound 8 (8.6 g, 95%).

MS: m/z: M$^+$ calculated for $C_{29}H_{23}F_6N_4O_2^+$, 573.17, found 573.21

[Example 9] Preparation of Diamine 9

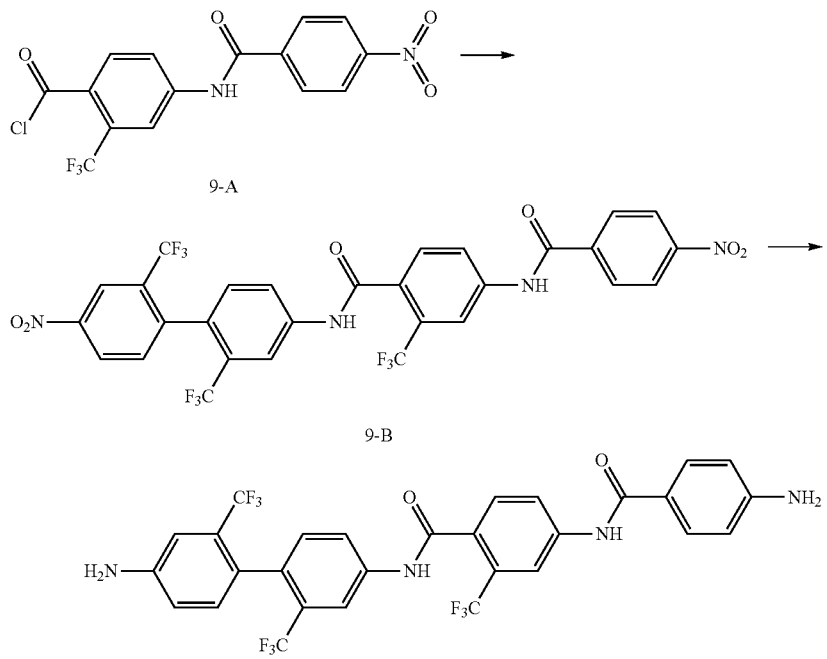

A diamine 9 (8.4 g, 92%) was prepared in the same manner as that of Example 8, except that 4-[(4-nitrobenzoyl)amino]-2-trifluoromethyl-benzoic acid was used instead of 4-[(4-nitrobenzoyl)amino]-2-methyl-benzoic acid.

MS: m/z: M$^+$ calculated for $C_{29}H_{20}F_9N_4O_2^+$, 627.14, found 627.20

Production of Polymer and Film

Example 10

N,N-dimethylacetamide (DMAc), 2,2'-bis(trifluoromethyl)benzidine (TFMB), and the diamine 1 prepared in Example 1 were added to a reactor in a nitrogen atmosphere, and the mixture was sufficiently dissolved. 1,2,3,4-cyclobutanetetracarboxylic dianhydride (CBDA) was added to the solution of TFMB/diamine 1, the mixture was sufficiently dissolved, 4,4'-(hexafluoroisopropylidene)diphthalic anhydride (6FDA) and terephthaloyl dichloride (TPC) were added, and then the mixture was stirred for 6 hours to be dissolved and reacted, thereby preparing a polyamic acid solution. At this time, as for the amount of each monomer, as shown in the composition ratio of Table 1, a molar ratio of TFMB:diamine 1:TPC:6FDA:CBDA was set to 50:50:

35:15:50 based on a ratio of 100 of the diamine raw material and a ratio of 100 of the other raw materials, the solid content was adjusted to 13 wt %, and the temperature in the reactor was maintained at 40° C. Subsequently, pyridine and acetic anhydride were added to the polyamic acid solution at 2.5 times the total mole of dianhydride, and the mixture was stirred at 60° C. for 12 hours. Thereafter, a solid obtained by precipitating the solution in an excessive amount of methanol and performing filtration was vacuum-dried at 50° C. for 12 hours or longer to obtain a powder. 10.45 g of the resulting powder was dissolved in 89.55 g of N,N-dimethylacetamide (DMAc) to prepare a composition for forming a film having a solid content of 10.45 wt %. The viscosity of the prepared composition was 64,000 cps.

Solution casting was performed on the composition for forming a film on a glass substrate using an applicator. Thereafter, primary drying was performed at 90° C. for 30 minutes using a convection oven, an additional heat treatment was performed under nitrogen conditions at 280° C. for 1 hour, cooling was performed to room temperature, and then a film formed on the glass substrate was separated from the substrate, thereby obtaining a film having a thickness of 51 μm. The physical properties of the film are shown in Tables 2 and 3.

Example 11

N,N-dimethylacetamide (DMAc) and 2,2'-bis(trifluoromethyl)benzidine (TFMB) were added to a reactor in a nitrogen atmosphere, the mixture was sufficiently stirred, terephthaloyl dichloride (TPC) was added, and then the mixture was stirred for 6 hours to be dissolved and reacted. Thereafter, the reaction product obtained by precipitation and filtration using an excessive amount of water was vacuum-dried at 90° C. for 6 hours or longer to obtain a polyamide oligomer.

DMAc, the polyamide oligomer, additional TFMB, and the diamine 1 obtained in Example 1 were added to the reactor in a nitrogen atmosphere again, and the total amount of the diamine used was set so that a molar ratio of TFMB:diamine 1 was 50:50. Thereafter, 1,2,3,4-cyclobutanetetracarboxylic dianhydride (CBDA) and 4,4'-(hexafluoroisopropylidene)diphthalic anhydride (6FDA) were sequentially added, and the mixture was stirred for 12 hours to be dissolved and reacted, thereby preparing a polyamic acid solution. At this time, as for the amount of each monomer, as shown in the composition ratio of Table 1, a molar ratio of TFMB:diamine 1:TPC:6FDA:CBDA was set to 50:50:35:20:45 based on a ratio of 100 of the diamine raw material and a ratio of 100 of the other raw materials, the solid content was adjusted to 13 wt %, and the temperature in the reactor was maintained at 40° C. Subsequently, pyridine and acetic anhydride were added to the polyamic acid solution at 2.5 times the total mole of dianhydride, and the mixture was stirred at 60° C. for 12 hours, thereby preparing a composition for forming a film. The viscosity of the prepared composition was 48,000 cps.

Solution casting was performed on the composition for forming a film on a glass substrate using an applicator. Thereafter, primary drying was performed at 90° C. for 30 minutes using a convection oven, an additional heat treatment was performed under nitrogen conditions at 280° C. for 1 hour, cooling was performed to room temperature, and then a film formed on the glass substrate was separated from the substrate, thereby obtaining a film having a thickness of 50 μm. The physical properties of the film are shown in Tables 2 and 3.

Examples 12 to 25

Films were obtained in the same manner as that of Example 10, except that the kind and the amounts of the monomers added were changed as shown in Table 1. The physical properties of the prepared samples were measured. The results thereof are shown in Tables 2 and 3.

Comparative Examples 1 to 7

Films were obtained in the same manner as that of Example 10, except that the kind and the amounts of the monomers added were changed as shown in Table 1. The physical properties of the prepared samples were measured. The results thereof are shown in Tables 2 and 3.

[Comparative Examples 8 and 13]

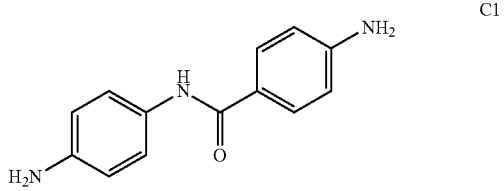

C1

Films were obtained in the same manner as that of Example 1, except that the diamine C1 was used instead of the diamine 1 and the amounts of the monomers added were changed as shown in Table 1. The physical properties of the prepared samples were measured. The results thereof are shown in Tables 2 and 3.

[Comparative Examples 9 and 10]

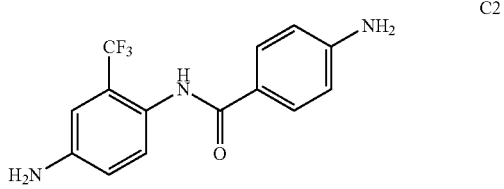

C2

Films were obtained in the same manner as that of Example 1, except that the diamine C2 was used instead of the diamine 1 and the amounts of the monomers added were changed as shown in Table 1. The physical properties of the prepared samples were measured. The results thereof are shown in Tables 2 and 3.

[Comparative Examples 11 and 12]

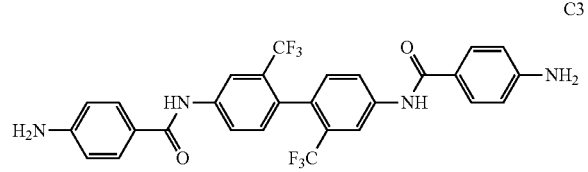

C3

Films were obtained in the same manner as that of Example 1, except that the diamine C3 was used instead of the diamine 1 and the amounts of the monomers added were changed as shown in Table 1. The physical properties of the prepared samples were measured. The results thereof are shown in Tables 2 and 3.

TABLE 1

| | Composition ratio (molar ratio) | | | | | | | | | | | |
|---|---|---|---|---|---|---|---|---|---|---|---|---|
| | TFMB | Diamine 1 | Diamine 2 | C1 | C2 | C3 | TPC | 6FDA | CBDA | BPAF | BPDA | Thickness (μm) |
| Example 10 | 50 | 50 | — | — | — | — | 35 | 15 | 50 | — | — | 51 |
| Example 11 | 50 | 50 | — | — | — | — | 35 | 20 | 45 | — | — | 50 |
| Example 12 | 70 | 30 | — | — | — | — | 50 | 15 | 35 | — | — | 50 |
| Example 13 | 77 | 23 | — | — | — | — | 55 | 15 | 30 | — | — | 48 |
| Example 14 | 80 | 20 | — | — | — | — | 55 | 15 | 30 | — | — | 48 |
| Example 15 | 80 | 20 | — | — | — | — | 55 | 10 | 35 | — | — | 48 |
| Example 16 | 90 | 10 | — | — | — | — | 50 | 15 | 35 | — | — | 50 |
| Example 17 | 90 | 10 | — | — | — | — | 35 | 15 | 50 | — | — | 49 |
| Example 18 | 90 | 10 | — | — | — | — | 70 | 15 | 15 | — | — | 50 |
| Example 19 | 50 | 50 | — | — | — | — | 35 | — | 50 | 15 | — | 50 |
| Example 20 | 70 | — | 30 | — | — | — | 50 | 15 | 35 | — | — | 46 |
| Example 21 | 90 | 10 | — | — | — | — | — | 85 | — | — | 15 | 48 |
| Example 22 | — | 100 | — | — | — | — | — | 100 | — | — | — | 55 |
| Example 23 | — | 100 | — | — | — | — | 70 | 30 | — | — | — | 50 |
| Example 24 | — | 100 | — | — | — | — | — | 80 | 20 | — | — | 48 |
| Example 25 | 50 | 50 | — | — | — | — | — | 80 | 20 | — | — | 49 |
| Comparative Example 1 | 100 | — | — | — | — | — | 55 | 15 | 30 | — | — | 50 |
| Comparative Example 2 | 100 | — | — | — | — | — | 70 | 15 | 15 | — | — | 50 |
| Comparative Example 3 | 100 | — | — | — | — | — | 55 | 20 | — | — | 25 | 51 |
| Comparative Example 4 | 100 | — | — | — | — | — | 50 | 15 | 35 | — | — | 50 |
| Comparative Example 5 | 100 | — | — | — | — | — | — | 80 | 20 | — | — | 48 |
| Comparative Example 6 | 100 | — | — | — | — | — | — | 100 | — | — | — | 55 |
| Comparative Example 7 | 100 | — | — | — | — | — | 70 | 30 | — | — | — | 48 |
| Comparative Example 8 | 70 | — | — | 30 | — | — | 50 | 15 | 35 | — | — | 50 |
| Comparative Example 9 | 70 | — | — | — | 30 | — | 50 | 15 | 35 | — | — | 48 |
| Comparative Example 10 | 80 | — | — | — | 20 | — | 55 | 15 | 30 | — | — | 50 |
| Comparative Example 11 | 70 | — | — | — | — | 30 | 50 | 15 | 35 | — | — | 50 |
| Comparative Example 12 | 50 | — | — | — | — | 50 | 35 | 15 | 50 | — | — | 50 |
| Comparative Example 13 | 50 | — | — | 50 | — | — | — | 80 | 20 | — | — | 50 |

Evaluation 1. Film Formability

Thicknesses of the films produced using the polymers according to Examples and Comparative Examples were measured three times each with a thin film thickness meter (p-bite, manufactured by TESA SA). The average values thereof are shown in Table 1.

In the cases of the films produced using the polymers of Examples, it could be confirmed that a film having a thickness sufficient to be used as a flexible window cover film was formed.

Evaluation 2. Yellow Index

The yellow indices of the films produced using the polymers according to Examples and Comparative Examples were measured. The results thereof are shown in Table 2.

TABLE 2

| | Yellow index | Evaluation |
|---|---|---|
| Example 10 | 4.7 | ○ |
| Example 11 | 4.5 | ○ |
| Example 12 | 4.4 | ○ |
| Example 13 | 3.5 | ○ |

TABLE 2-continued

| | Yellow index | Evaluation |
|---|---|---|
| Example 14 | 3.0 | ○ |
| Example 15 | 3.6 | ○ |
| Example 16 | 3.1 | ○ |
| Example 17 | 4.0 | ○ |
| Example 18 | 3.0 | ○ |
| Example 19 | 3.6 | ○ |
| Comparative Example 1 | 2.7 | ○ |
| Comparative Example 2 | 2.5 | ○ |
| Comparative Example 3 | 4.6 | ○ |
| Comparative Example 4 | 2.6 | ○ |

TABLE 2-continued

|  | Yellow index | Evaluation |
| --- | --- | --- |
| Comparative Example 5 | 1.7 | ○ |
| Comparative Example 6 | 1.7 | ○ |
| Comparative Example 7 | 2.4 | ○ |
| Comparative Example 8 | 16.6 | X |
| Comparative Example 9 | 6.3 | X |
| Comparative Example 10 | 5.4 | X |
| Comparative Example 11 | 5.6 | X |
| Comparative Example 12 | 5.2 | X |
| Comparative Example 13 | 16.8 | X |

As shown in Table 2, in the cases of the films of Examples including a structural unit derived from the diamine according to an exemplary embodiment, it could be confirmed that an excellent yellow index applicable to a cover window, a substrate material, or the like of a display device was implemented. On the other hand, in the cases of the films of Comparative Examples 8 to 13 produced using the diamines (C1 to C3) having no biphenyl group and/or asymmetric structure, it could be confirmed that the yellow index was significantly deteriorated in comparison to the films of Examples in which the molar ratio of the monomer and the heat treatment temperature were the same as those of the films of Comparative Examples 8 to 13. Accordingly, it could be confirmed that the films of Comparative Examples 8 to 13 were not suitable for application as a cover window, a substrate material, or the like of a display device.

The optical properties and the mechanical properties of the films having an excellent yellow index of Examples and Comparative Examples were measured. The results thereof are shown in Table 3.

Evaluation 3. Optical Properties and Mechanical Properties

TABLE 3

|  | Transmittance (%) | Haze (%) | Modulus (GPa) |
| --- | --- | --- | --- |
| Example 10 | 89.2 | 0.8 | 8.0 |
| Example 11 | 89.0 | 0.6 | 7.5 |
| Example 12 | 89.6 | 0.8 | 7.8 |
| Example 13 | 90.0 | 0.6 | 7.5 |
| Example 14 | 89.7 | 0.3 | 7.6 |
| Example 15 | 89.5 | 0.6 | 7.7 |
| Example 16 | 90.3 | 0.5 | 7.4 |
| Example 17 | 90.1 | 0.3 | 7.5 |
| Example 18 | 89.0 | 0.8 | 7.2 |
| Example 19 | 89.3 | 0.5 | 8.3 |
| Comparative Example 1 | 90.5 | 0.3 | 6.9 |
| Comparative Example 2 | 89.7 | 0.3 | 6.6 |
| Comparative Example 3 | 90.3 | 0.3 | 5.8 |
| Comparative Example 4 | 90.5 | 0.3 | 6.8 |
| Comparative Example 5 | 91.3 | 0.4 | 4.0 |
| Comparative Example 6 | 91.4 | 0.4 | 3.8 |
| Comparative Example 7 | 90.1 | 0.6 | 5.9 |

Referring to Table 3, in the cases of the films including a structural unit derived from the diamine according to an exemplary embodiment of Examples, it could be confirmed that the yellow index was low, the transmittance and the haze were equivalent to or superior to those of the films of Comparative Examples 1 to 7, and the modulus was significantly increased.

In summary, since the diamine according to an exemplary embodiment has a biphenyl group structure, an asymmetric structure, and an amide bond, when the diamine is used as a monomer, it is possible to produce a polyimide-based film having significantly improved mechanical properties while maintaining excellent optical properties.

As set forth above, excellent optical properties and mechanical properties of the polyimide-based film produced using the diamine according to an exemplary embodiment may be simultaneously implemented.

Specifically, the diamine according to an exemplary embodiment has a structure having both a unit capable of improving mechanical properties of the polyimide-based film and a unit capable of reducing a charge transfer complex (CTC) effect, such that it is possible to more effectively improve the mechanical properties of the polyimide-based film without deterioration of the yellow index and the transparency of the polyimide-based film.

Further, the diamine according to an exemplary embodiment and the polymer produced using the same may have excellent solution handleability, such that production processability may be improved, and it is possible to produce a film having a sufficient thickness.

That is, the diamine according to an exemplary embodiment may provide a polyimide-based film that is colorless and transparent and has a high modulus, excellent mechanical strength, and excellent production processability, and thus, may be applied to various industrial fields including a display device.

Hereinabove, although the present invention has been described by specific matters and limited exemplary embodiments, they have been provided only for assisting in the entire understanding of the present invention. Therefore, the present invention is not limited to the exemplary embodiments. Various modifications and changes may be made by those skilled in the art to which the present invention pertains from this description.

Therefore, the spirit of the present invention should not be limited to the described exemplary embodiments, but the claims and all modifications equal or equivalent to the claims are intended to fall within the spirit of the present invention.

What is claimed is:

1. A diamine represented by the following Chemical Formula 1:

[Chemical Formula 1]

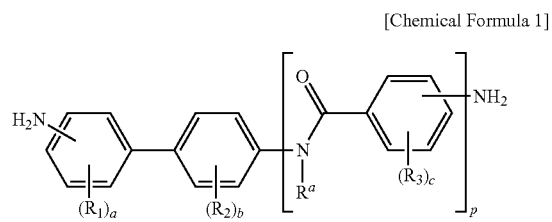

where in Chemical Formula 1, $R_1$ and $R_2$ are each independently (C2-C20) alkyl, (C1-C20) alkoxy, halo (C1-C20) alkyl, (C1-C20) alkylcarbonyl, (C1-C20) alkoxycarbonyl, (C6-C20) arylcarbonyl, tri(C1-C20) alkylsilyl, carboxyl, hydroxy, amino, nitro, cyano, or halogen;

$R_3$ is (C1-C20) alkyl, (C1-C20) alkoxy, halo (C1-C20) alkyl, (C1-C20) alkylcarbonyl, (C1-C20) alkoxycarbonyl, (C6-C20) arylcarbonyl, tri(C1-C20) alkylsilyl, carboxyl, hydroxy, amino, nitro, cyano, or halogen;

$R^a$ is hydrogen, (C1-C20) alkyl, or (C6-C20) aryl;

a and b are each independently an integer of 1 to 4;

c is an integer of 0 to 4;

when a, b, and c are integers of 2 or more, $R_1$, $R_2$, and $R_3$ may be the same as or different from each other; and p is an integer of 1 to 3.

2. The diamine of claim 1, wherein the diamine represented by Chemical Formula 1 is represented by the following Chemical Formula 2 or 3:

[Chemical Formula 2]

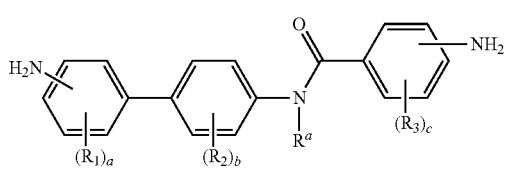

[Chemical Formula 3]

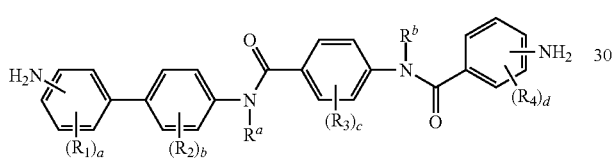

where in Chemical Formulas 2 and 3, $R_1$ and $R_2$ are each independently (C2-C7) alkyl, (C1-C7) alkoxy, halo (C1-C7) alkyl, (C1-C7) alkylcarbonyl, (C1-C7) alkoxycarbonyl, (C6-C12) arylcarbonyl, tri (C1-C7) alkylsilyl, carboxyl, hydroxy, amino, nitro, cyano, or halogen;

$R_3$ and $R_4$ are each independently (C1-C7) alkyl, (C1-C7) alkoxy, halo (C1-C7) alkyl, (C1-C7) alkylcarbonyl, (C1-C7) alkoxycarbonyl, (C6-C12) arylcarbonyl, tri (C1-C7) alkylsilyl, carboxyl, hydroxy, amino, nitro, cyano, or halogen;

$R^a$ and $R^b$ are each independently hydrogen, (C1-C7) alkyl, or (C6-C12) aryl;

a and b are each independently an integer of 1 to 3;

c and d are each independently an integer of 0 to 3; and when a, b, c, and d are integers of 2 or more, $R_1$, $R_2$, $R_3$, and $R_4$ may be the same as or different from each other.

3. The diamine of claim 1, wherein the diamine represented by Chemical Formula 1 is represented by the following Chemical Formula 4 or 5:

[Chemical Formula 4]

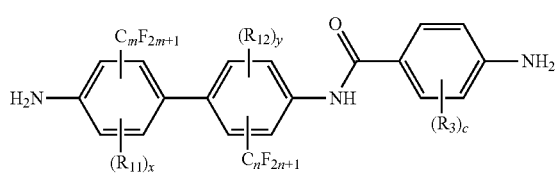

[Chemical Formula 5]

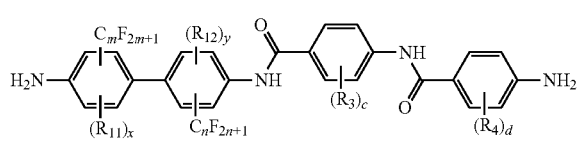

where in Chemical Formulas 4 and 5, $R_3$ and $R_4$ are each independently (C1-C7) alkyl, (C1-C7) alkoxy, halo (C1-C7) alkyl, carboxyl, hydroxy, amino, or halogen;

$R_{11}$ and $R_{12}$ are each independently (C2-C7) alkyl, halo (C1-C7) alkyl, or halogen;

n and m are each independently an integer of 1 to 5;

x, y, c, and d are each independently an integer of 0 to 2; and when x, y, c, and d are 2, $R_{11}$, $R_{12}$, $R_3$, and $R_4$ may be the same as or different from each other.

4. The diamine of claim 1, wherein the diamine represented by Chemical Formula 1 is represented by the following Chemical Formula 6 or 7:

[Chemical Formula 6]

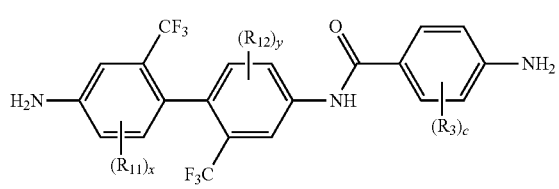

[Chemical Formula 7]

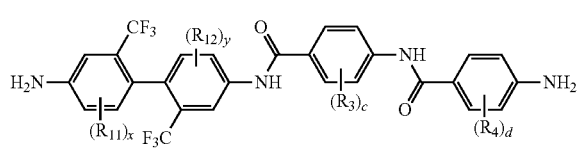

where in Chemical Formulas 6 and 7, $R_3$ and $R_4$ are each independently (C1-C5) alkyl, (C1-C5) alkoxy, halo (C1-C5) alkyl, carboxyl, hydroxy, amino, or halogen;

$R_{11}$ and $R_{12}$ are each independently (C2-C5) alkyl, halo (C1-C5) alkyl, or halogen;

x, y, and d are each independently 0 or 1;

c is an integer of 0 to 2; and when c are 2, $R_3$ may be the same as or different from each other.

5. The diamine of claim 4, wherein the diamine is selected from the following compounds:

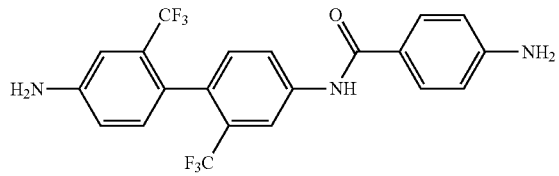

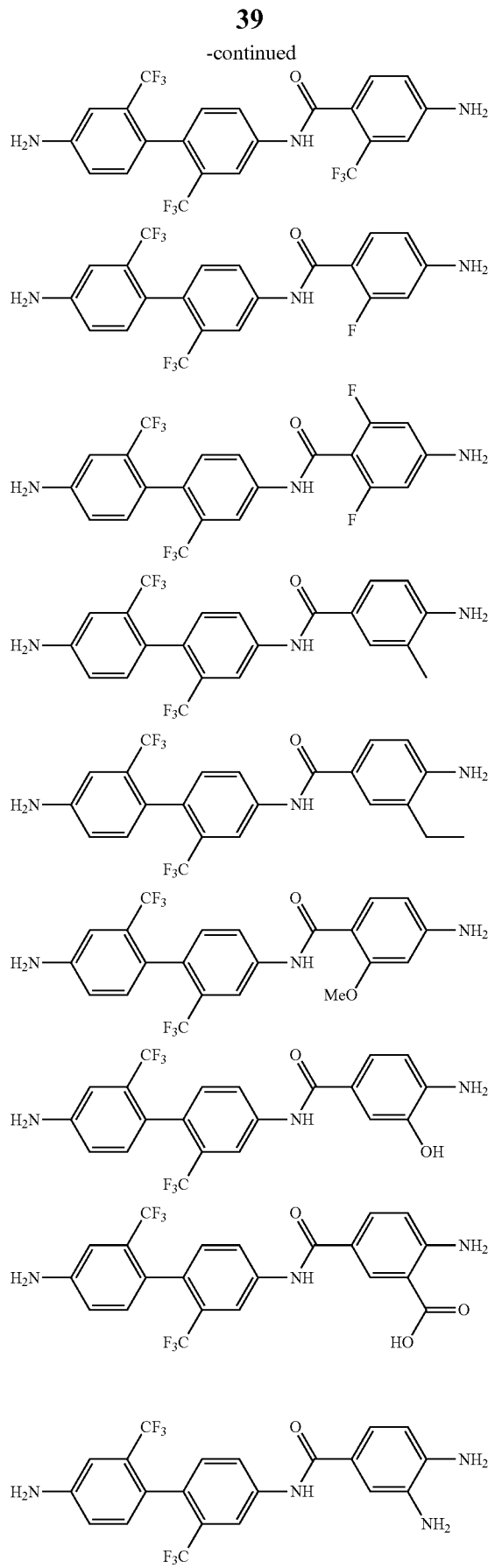

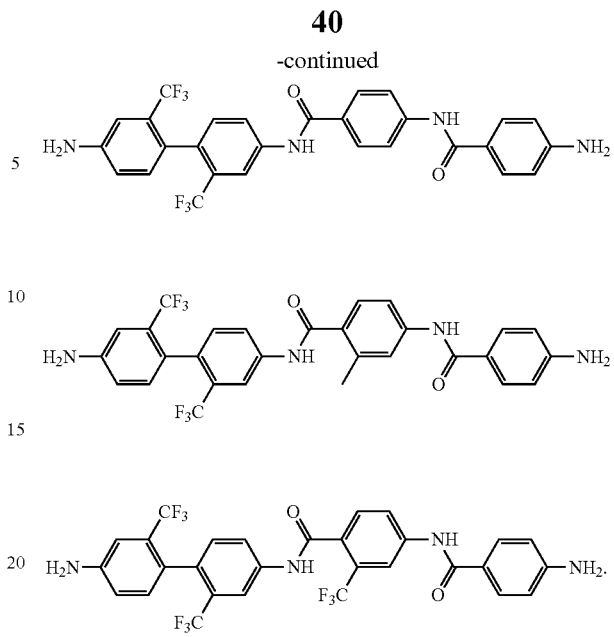

6. A method of preparing a diamine, the method comprising preparing a diamine represented by the following Chemical Formula 1 by reducing a compound represented by the following Chemical Formula A under a reduction catalyst:

[Chemical Formula 1]

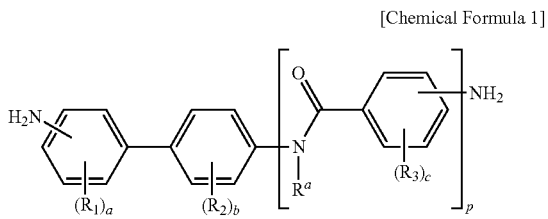

[Chemical Formula A]

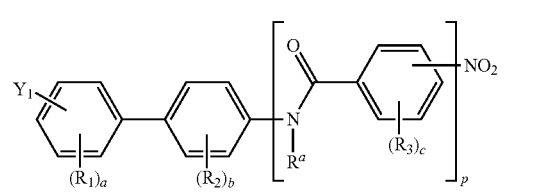

where in Chemical Formulas 1 and A, $Y_1$ is nitro or amino; and the definitions of $R_1$ to $R_3$, $R^a$, a, b, c, and p are the same as those in Chemical Formula 1 of claim 1.

7. The method of claim 6, wherein the reduction catalyst is selected from Zn, Cu, Ag, Au, Cd, Hg, Fe, $K_4[Fe(CN)_6]$, $NaBH_4$, and a combination thereof.

8. The method of claim 7, wherein the reduction catalyst further comprises a cocatalyst selected from $NH_4Cl$, $H_2CO_3$, $H_3PO_4$, HCl, $CH_3COOH$, and a combination thereof.

9. The method of claim 6, wherein the compound represented by Chemical Formula A is prepared by reacting $Y_2$ of a compound represented by the following Chemical Formula A-1 with X of a compound represented by the following Chemical Formula A-2:

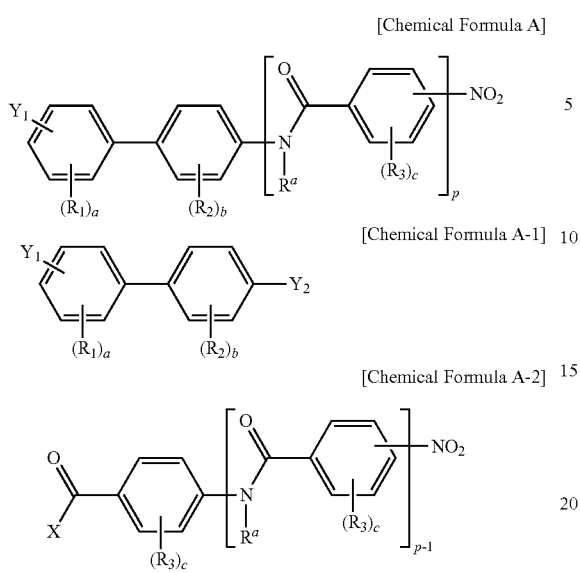

where in Chemical Formulas A, A-1, and A-2,
X is halogen;
$Y_1$ is nitro or amino;
$Y_2$ is $$*\text{——NHR}^a \quad \text{or} \quad *\text{——}\overset{+}{\text{NH}}_2 R^a;$$

$R_1$ and $R_2$ are each independently (C2-C20) alkyl, (C1-C20) alkoxy, halo (C1-C20) alkyl, (C1-C20) alkylcarbonyl, (C1-C20) alkoxycarbonyl, (C6-C20) arylcarbonyl, tri(C1-C20) alkylsilyl, carboxyl, hydroxy, amino, nitro, cyano, or halogen;

$R_3$ is (C1-C20) alkyl, (C1-C20) alkoxy, halo (C1-C20) alkyl, (C1-C20) alkylcarbonyl, (C1-C20) alkoxycarbonyl, (C6-C20) arylcarbonyl, tri(C1-C20) alkylsilyl, carboxyl, hydroxy, amino, nitro, cyano, or halogen;

$R^a$ is hydrogen, (C1-C20) alkyl, or (C6-C20) aryl;
a and b are each independently an integer of 1 to 4;
c is an integer of 0 to 4;
when a, b, and c are integers of 2 or more, $R_1$, $R_2$, and $R_3$ may be the same as or different from each other; and
p is an integer of 1 to 3.

10. A polymer comprising a unit derived from the diamine of claim 1; and a unit derived from a dianhydride, a unit derived from an aromatic diacid dichloride, or a combination thereof.

11. The polymer of claim 10, wherein the dianhydride comprises an aromatic dianhydride, an alicyclic dianhydride, or a combination thereof.

12. The polymer of claim 10, wherein the dianhydride comprises a fluorine-based aromatic dianhydride and an alicyclic dianhydride.

13. The polymer of claim 10, wherein the aromatic diacid dichloride comprises terephthaloyl dichloride, isophthaloyl dichloride, 1,1'-biphenyl-4,4'-dicarbonyl dichloride, 1,4-naphthalenedicarboxylic dichloride, 2,6-naphthalenedicarboxylic dichloride, 1,5-naphthalenedicarboxylic dichloride, 4,4'-oxybis(benzoyl chloride), or a combination thereof.

14. A composition for forming a film, comprising the polymer of claim 10.

15. A film produced using the composition for forming a film of claim 14.

16. The film of claim 15, wherein the film comprises polyimide, polyamide, or a combination thereof.

17. The film of claim 16, wherein a thickness of the film is 1 to 500 um.

18. The film of claim 17, wherein the film has a yellow index (YI) of 10 or less when measured according to ASTM E313, a haze of 2.0% or less when measured according to ASTM D1003, and a total light transmittance of 80% or more when measured according to ASTM D1003.

19. The film of claim 17, wherein the film has a modulus of 5 GPa or more when measured according to ASTM D882.

20. A multi-layer structure comprising the film of claim 15.

21. A display device comprising the film of claim 15.

* * * * *